(12) United States Patent
Buchwald et al.

(10) Patent No.: US 9,972,791 B2
(45) Date of Patent: May 15, 2018

(54) [2.2]PARACYCLOPHANE-DERIVED DONOR/ACCEPTOR-TYPE MOLECULES FOR OLED APPLICATIONS

(71) Applicant: Massachusetts Institute of Technology, Cambridge, MA (US)

(72) Inventors: Stephen L. Buchwald, Newton, MA (US); Wenliang Huang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 63 days.

(21) Appl. No.: 15/172,623

(22) Filed: Jun. 3, 2016

(65) Prior Publication Data

US 2016/0359118 A1 Dec. 8, 2016

Related U.S. Application Data

(60) Provisional application No. 62/171,411, filed on Jun. 5, 2015.

(51) Int. Cl.

| | | |
|---|---|---|
| *H01L 51/00* | (2006.01) | |
| *C07D 487/08* | (2006.01) | |
| *C09K 11/06* | (2006.01) | |
| *C07D 209/94* | (2006.01) | |
| *C07D 403/10* | (2006.01) | |
| *C08G 61/02* | (2006.01) | |
| *C08G 61/12* | (2006.01) | |
| *C08G 73/06* | (2006.01) | |
| *H01L 51/52* | (2006.01) | |
| *H01L 51/50* | (2006.01) | |
| *H01L 51/05* | (2006.01) | |

(52) U.S. Cl.
CPC ........ *H01L 51/0072* (2013.01); *C07D 209/94* (2013.01); *C07D 403/10* (2013.01); *C07D 487/08* (2013.01); *C08G 61/02* (2013.01); *C08G 61/124* (2013.01); *C09K 11/06* (2013.01); *H01L 51/0035* (2013.01); *H01L 51/0067* (2013.01); *C08G 73/0672* (2013.01); *C08G 2261/143* (2013.01); *C08G 2261/146* (2013.01); *C08G 2261/148* (2013.01); *C08G 2261/149* (2013.01); *C08G 2261/5222* (2013.01); *C08G 2261/95* (2013.01); *C09K 2211/1007* (2013.01); *C09K 2211/1029* (2013.01); *C09K 2211/1033* (2013.01); *C09K 2211/1037* (2013.01); *C09K 2211/1051* (2013.01); *C09K 2211/1059* (2013.01); *C09K 2211/1466* (2013.01); *H01L 51/0558* (2013.01); *H01L 51/5012* (2013.01); *H01L 51/5024* (2013.01); *H01L 51/5206* (2013.01); *H01L 51/5221* (2013.01)

(58) Field of Classification Search
CPC ............. H01L 51/0072; H01L 51/0067; H01L 51/0035; H01L 51/5206; C07D 487/08; C07D 403/10; C07D 209/94; C09K 11/06; C09K 2211/1029; C09K 2211/1007; C09K 2211/1059; C08G 73/0672; C08G 61/02; C08G 61/124
USPC ......................................................... 428/690
See application file for complete search history.

(56) References Cited

U.S. PATENT DOCUMENTS

| | | | | |
|---|---|---|---|---|
| 2013/0137818 A1* | 5/2013 | Schulte | .................. | C08G 61/12 524/612 |
| 2016/0163989 A1* | 6/2016 | Yang | .................. | H01L 51/0059 257/40 |

OTHER PUBLICATIONS

Lennatz et al. "Synthesis of Planar Chiral Carbazole Derivatives Bearing a [2.2]Paracyclophane Skeleton", Israel Journal of Chemistry, 2012, vol. 52, issue 1-2, 171-179.*
International Search Report and Written Opinion for International Application No. PCT/US16/35655 dated Oct. 31, 2016.
Lennartz, et al., "Synthesis of Planar Chiral Carbazole Derivatives Bearing a [2.2] Paracyclophane Skeleton," Israel J Chem, 52(1-2): 171-179 (2012).

* cited by examiner

*Primary Examiner* — Michael M Bernshteyn
(74) *Attorney, Agent, or Firm* — Dana M. Gordon; Foley Hoag LLP

(57) ABSTRACT

Disclosed are [2.2]paracyclophane-derivative compounds and related polymers that are useful as stable, efficient, blue-light emitting compounds for OLED applications.

26 Claims, 7 Drawing Sheets o-PCP-2Cz-2A    PCP-Cz-A    g-PCP-2Cz-2A p-PCP-2Cz-2A    m-PCP-2Cz-2A $\Delta E_{ST} = 0.6$ eV
$\tau = 454$ μs $\Delta E_{ST} = 0.1$ eV
$\tau = 3.67$ μs

[2.2]PARACYCLOPHANE-DERIVED DONOR/ACCEPTOR-TYPE MOLECULES FOR OLED APPLICATIONS

RELATED APPLICATION

This application claims the benefit of priority to U.S. Provisional Patent Application Ser. No. 62/171,411, filed Jun. 5, 2015, the contents of which are hereby incorporated by reference.

BACKGROUND

Organic light-emitting diode (OLED) technology has been widely used to create digital displays in high resolution televisions, computer monitors, and handheld devices. The use of OLED technology provides advantages over other techniques, such as liquid-crystal display (LCD) technology, in various measures, such as energy efficiency, color contrast, resolution, and weight. A typical OLED display combines three basic colors—red, green, and blue—generated by electroluminescence of emitting materials.

Both fluorescent and phosphorescent materials have been developed as emitting materials. In principle, phosphorescent materials can achieve higher quantum efficiency than fluorescent materials because electroluminescent materials generate singlet-to-triplet excitation states in an intrinsic ratio of 1:3. Because of their relative increased quantum efficiency, noble metal-based phosphorescent molecules have been used as highly efficient and stable red and green light-emitting sources for OLED applications. However, phosphorescent materials that emit blue light have been found to be inefficient and unstable because of the highly energetic nature of excited states in blue light-emitting sources.

As an alternative, fluorescent materials minimize the lifetime of high-energy excited states, thereby resulting in a much faster light-emission process. However, as mentioned above, the intrinsic nature of electroluminescence limits the theoretical quantum efficiency of traditional fluorescent materials to 25%. Moreover, the other 75% of excited states (i.e., triplet excited states) can cause decomposition and, thus, undermine long-term stability of the material.

Thermally activated delayed fluorescence (TADF) can be used to address the efficiency and stability problems associated with fluorescent materials. TADF involves reverse intersystem crossing from triplet excited state to singlet excited state, which increases the theoretical quantum efficiency of fluorescence to a level comparable to phosphorescent materials. In addition, fast photo decay through the TADF process decreases the quantity as well as the lifetime of triplet excited states generated by excitons. To achieve TADF, a molecule must meet the standard general criteria for fluorescing, such as rigid structure to minimize non-radioactive decay, and also must have a small energy difference between its singlet and triplet excited states. Also, in order to achieve blue light emission, a compound must have a large energy gap between its highest occupied molecular orbital (HOMO) and lowest unoccupied molecular orbital (LUMO).

Despite some successes in developing red- and green-emitting TADF materials, a highly efficient and stable blue-emitting TADF source has not been discovered. There exists a need for a new class of stable, efficient, blue-light emitting compounds for OLED applications.

SUMMARY

In certain embodiments, the invention relates to a compound of formula Ia or formula Ib:

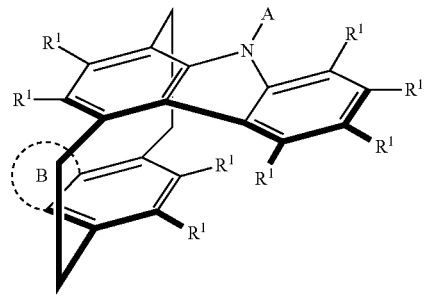
Formula Ia

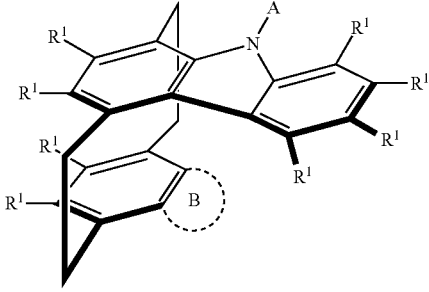
Formula Ib wherein

A is an aromatic moiety substituted with at least one electron-withdrawing substituent or a heteroaromatic moiety substituted with at least one electron-withdrawing substituent;

$R^1$ is, independently for each occurrence, hydrogen or alkyl; and

B is absent or an optionally substituted heteroaromatic moiety.

In certain embodiments, the invention relates to a compound of formula IIa', formula IIb', or formula IIc':

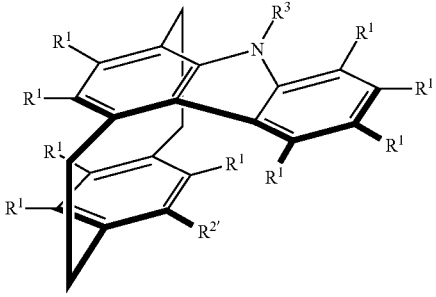
Formula IIa'

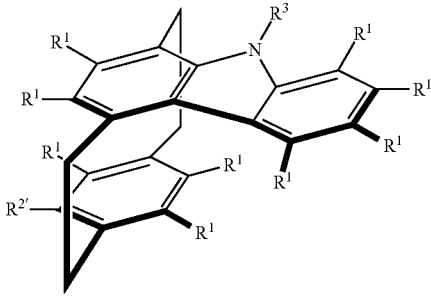
Formula IIb'

-continued

Formula IIc′

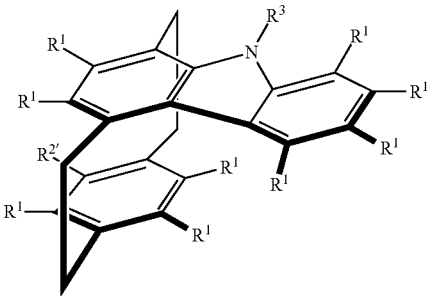

wherein
R¹ is, independently for each occurrence, hydrogen or alkyl;
R²′ is substituted or unsubstituted triazinyl, substituted or unsubstituted phenyl, substituted or unsubstituted pyridyl, substituted or unsubstituted pyrimidyl, or an electron-withdrawing group; and
R³ is hydrogen, alkyl, an optionally substituted aromatic moiety, or an optionally substituted heteroaromatic moiety.

In certain embodiments, the invention relates to a compound of formula IIa, formula IIb, or formula IIc:

Formula IIa

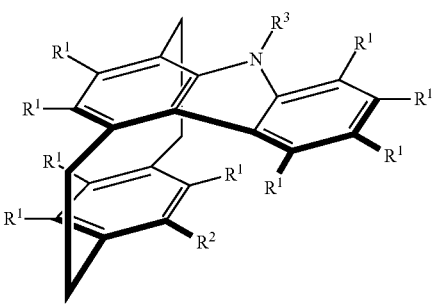

Formula IIb

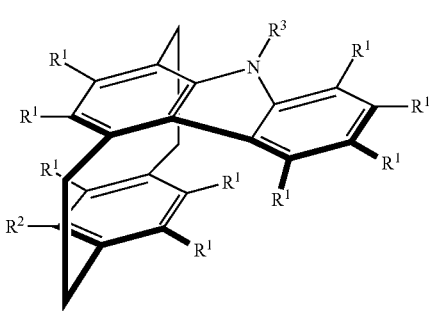

Formula IIc

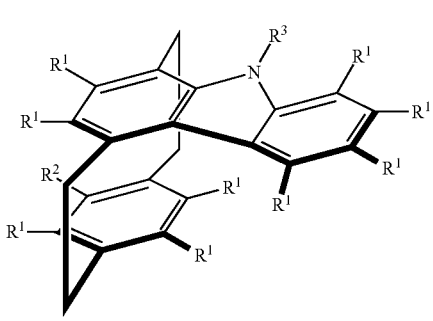

wherein
R¹ is, independently for each occurrence, hydrogen or alkyl;
R² is substituted or unsubstituted triazinyl or substituted or unsubstituted phenyl; and R³ is hydrogen, alkyl, an optionally substituted aromatic moiety, or an optionally substituted heteroaromatic moiety.

In certain embodiments, the invention relates to a compound of formula IIIa′, formula IIIb′, or formula IIIc′:

Formula IIIa′

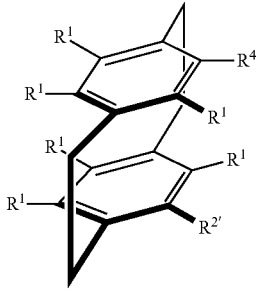

Formula IIIb′

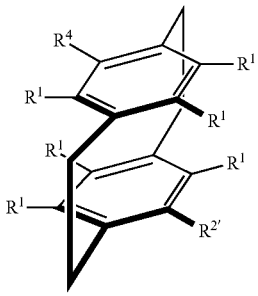

Formula IIIc′

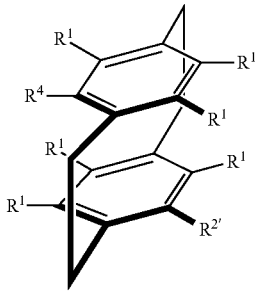

wherein
R¹ is, independently for each occurrence, hydrogen or alkyl;
R²′ is substituted or unsubstituted triazinyl, substituted or unsubstituted phenyl, substituted or unsubstituted pyridyl, substituted or unsubstituted pyrimidyl, or an electron-withdrawing group; and
R⁴ is hydrogen or an electron-donating group.

In certain embodiments, the invention relates to a compound of formula IIIa, formula IIIb, or formula IIIc:

Formula IIIa

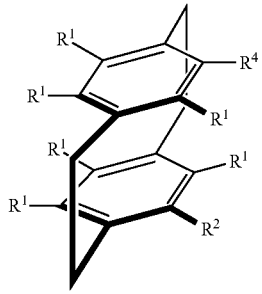

-continued

Formula IIIb

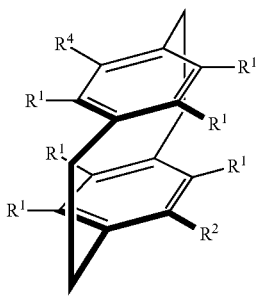

Formula IIIc

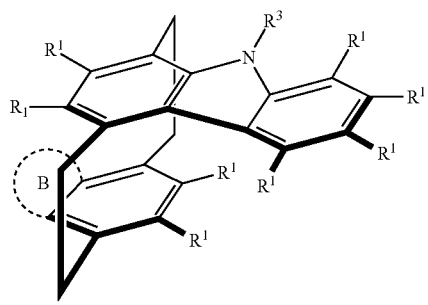

wherein

R¹ is, independently for each occurrence, hydrogen or alkyl;

R² is substituted or unsubstituted triazinyl or substituted or unsubstituted phenyl; and R⁴ is hydrogen or an electron-donating group.

In certain embodiments, the invention relates to a compound of formula IVa or formula IVb:

Formula IVa

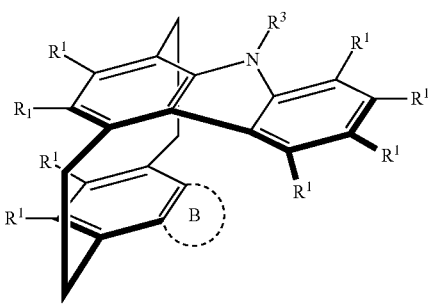

Formula IVb wherein

R¹ is, independently for each occurrence, hydrogen or alkyl;

B is absent or an optionally substituted heteroaromatic moiety; and

R³ is hydrogen, alkyl, an optionally substituted aromatic moiety, or an optionally substituted heteroaromatic moiety.

In certain embodiments, the invention relates to a compound of formula Va or formula Vb:

Formula Va

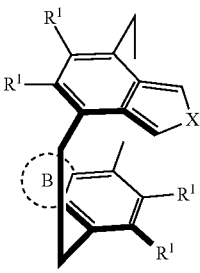

Formula Vb

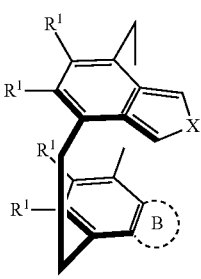

wherein

R¹ is, independently for each occurrence, hydrogen or alkyl;

B is absent or an optionally substituted heteroaromatic moiety;

X is O, S, or NR³; and

R³ is hydrogen, alkyl, an optionally substituted aromatic moiety, or an optionally substituted heteroaromatic moiety.

In certain embodiments, the invention relates to a polymer comprising a repeat unit of formula VIa or formula VIb:

Formula VIa

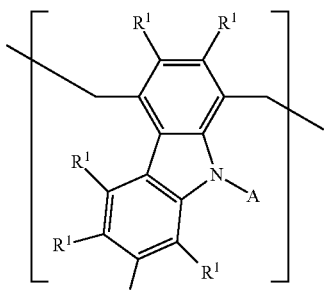

Formula VIb

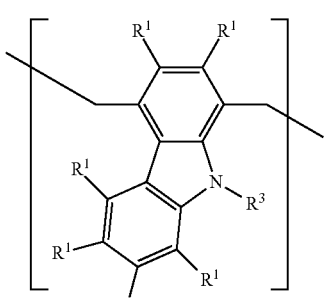

wherein, independently for each occurrence,

A is an aromatic moiety substituted with at least one electron-withdrawing substituent or a heteroaromatic moiety substituted with at least one electron-withdrawing substituent;

$R^1$ is, independently for each occurrence, hydrogen or alkyl; and $R^3$ is hydrogen, alkyl, an optionally substituted aromatic moiety, or an optionally substituted heteroaromatic moiety.

In certain embodiments, the invention relates to an electronic device, such as an OLED, comprising an anode, a cathode, and an emissive layer, wherein the emissive layer is disposed between the anode and the cathode; and the emissive layer comprises any of the compounds or any of the polymers described herein.

In certain embodiments, the invention relates to a method of producing visible light comprising applying a charge to any of the electronic devices described herein.

BRIEF DESCRIPTION OF THE FIGURES

FIG. 4C depicts a schematic structural diagram showing an electronic device of the invention.

FIG. 4D depicts a schematic structural diagram showing an electronic device of the invention.

DETAILED DESCRIPTION

Overview

In certain embodiments, the invention relates to [2.2] paracyclophane-derived donor-acceptor type compounds.

Figure 1:
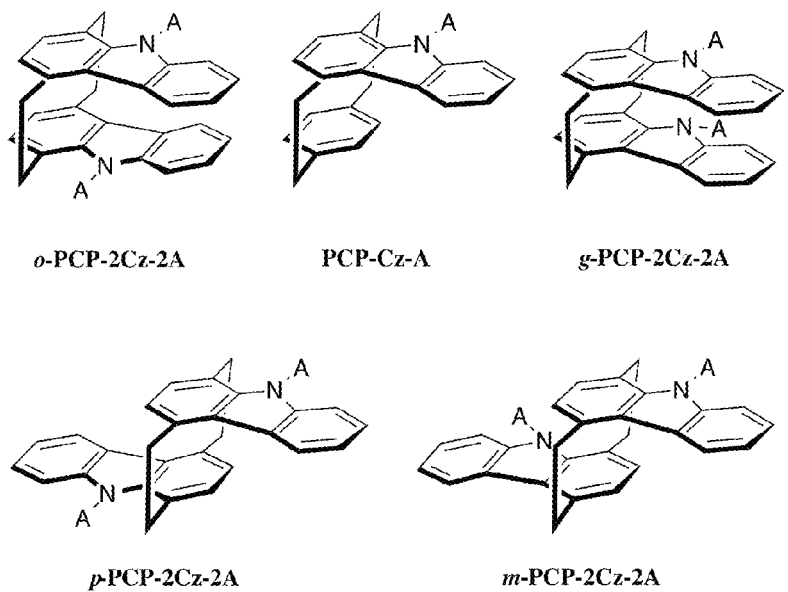
FIG. 1 depicts the chemical structures of five sub-classes of [2.2]paracylophane-derived carbazoles with attached acceptors (labeled as A in the drawing).
Figure 2:
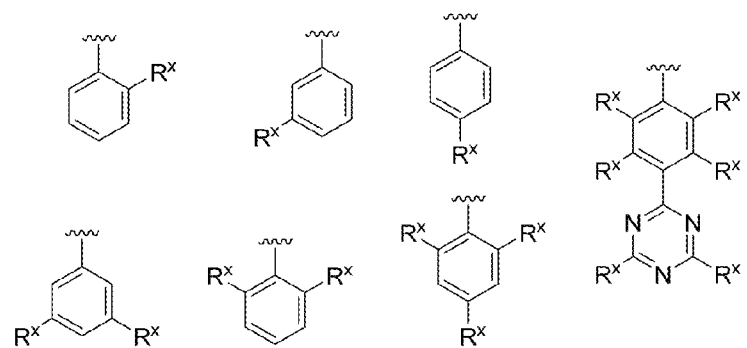
FIG. 2 depicts the chemical structure of representative acceptor moieties.

FIG. 1 depicts the general structures of a number of exemplary classes of compounds of the invention. In certain embodiments, the invention relates to one of five different sub-classes of compound, that is, mono-, ortho-, geminal-, para-, and meta-[2.2]paracylophane-carbazole derivatives. In certain embodiments, the compound is substituted with an acceptor moiety. Representative acceptor moieties are shown in FIG. 2.

[2.2]Paracylophane has a unique structure. The two phenyl rings are forced in close proximity, which leads to their distortion from planarity. The distortion from planarity energetically disfavors local triplet excited states, which, in turn, increases the quantum efficiency of emission.

In addition, despite high ring strain, a [2.2]paracylophane has high kinetic stability because there is no decomposition pathway with a low activation barrier. In fact, the only decomposition pathway involves breaking one or two carbon-carbon single bonds between two benzylic carbon atoms. Therefore, most compounds having a [2.2]paracyclophane core structure are stable to moderate heat and chemical conditions. For example, decomposition of underivatized [2.2]paracyclophane occurs only at high temperature (>350° C.) and under reduced pressure.

High thermal stability is crucial for late-stage manufacturing of large-size OLED displays because the chemical vapor deposition (CVD) process used in fabrication usually requires heat and vacuum conditions. In addition, molecules having a [2.2]paracylophane core structure exhibit good luminescence properties in the solid state for at least two reasons: intermolecular interactions are disfavored by (i) the π-π stacking interaction between the two phenyl rings, and (ii) the overall geometry of the molecule.

Figure 3A:
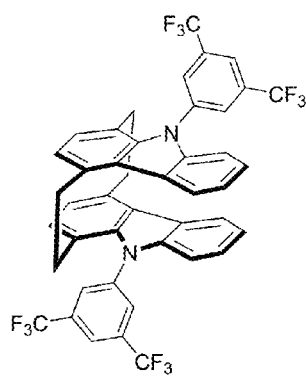
FIG. 3A shows preliminary results from evaluation in a device of [2.2]paracyclophane derived molecules without TADF properties.
Figure 3A:
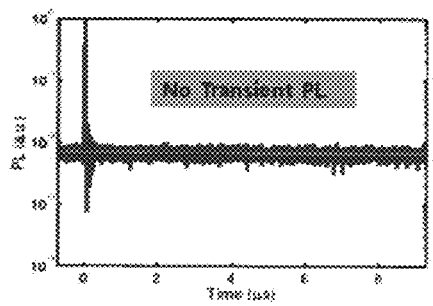
Figure 3B:
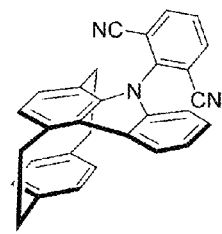
FIG. 3B shows preliminary results from evaluation in a device of [2.2]paracyclophane derived molecules with TADF properties.
Figure 3B:
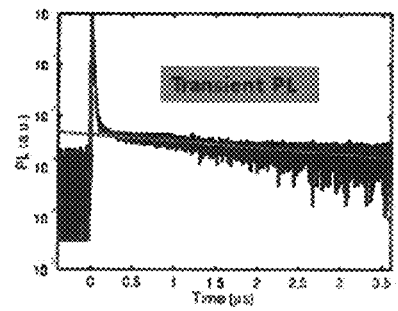

In certain embodiments, the invention relates to compounds exhibiting TADF properties (FIG. 3B). In certain embodiments, the short lifetime for delayed fluorescence is comparable to state-of-art green emitting TADF materials.

In certain embodiments, the invention relates to a method of synthesizing any compound described herein by palladium-catalyzed carbon-nitrogen bond and carbon-carbon bond formation reactions. In certain embodiments, the invention relates to a method of synthesizing any compound described herein by using a one-step carbon-nitrogen bond-forming reaction to couple an acceptor moiety, such as a phenyl derivative or a triazine, to a carbazole moiety.

Exemplary Compounds

In certain embodiments, the invention relates to a compound of formula Ia or formula Ib:

Formula Ia

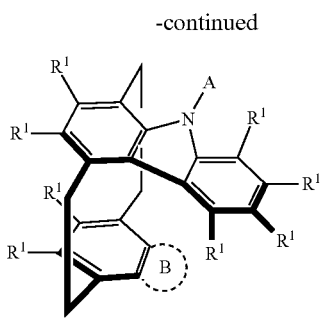

Formula Ib wherein

A is an aromatic moiety substituted with at least one electron-withdrawing substituent or a heteroaromatic moiety substituted with at least one electron-withdrawing substituent;

$R^1$ is, independently for each occurrence, hydrogen or alkyl; and

B is absent or an optionally substituted heteroaromatic moiety.

In certain embodiments, the invention relates to any one of the compounds described herein, wherein A is an aromatic moiety substituted with at least one electron-withdrawing substituent.

In certain embodiments, the invention relates to any one of the compounds described herein, wherein A is a heteroaromatic moiety substituted with at least one electron-withdrawing substituent.

In certain embodiments, the invention relates to any one of the compounds described herein, wherein A is phenyl substituted with at least one electron-withdrawing substituent.

In certain embodiments, the invention relates to any one of the compounds described herein, wherein A is phenyl substituted with one electron-withdrawing substituent. In certain embodiments, the invention relates to any one of the compounds described herein, wherein A is phenyl substituted with two electron-withdrawing substituents. In certain embodiments, the invention relates to any one of the compounds described herein, wherein A is phenyl substituted in the 3-position with an electron-withdrawing substituent. In certain embodiments, the invention relates to any one of the compounds described herein, wherein A is phenyl substituted in the 5-position with an electron-withdrawing substituent. In certain embodiments, the invention relates to any one of the compounds described herein, wherein A is phenyl substituted in the 2-position with an electron-withdrawing substituent. In certain embodiments, the invention relates to any one of the compounds described herein, wherein A is phenyl substituted in the 6-position with an electron-withdrawing substituent. In certain embodiments, the invention relates to any one of the compounds described herein, wherein A is phenyl substituted in the 4-position with an electron-withdrawing substituent.

In certain embodiments, the invention relates to any one of the compounds described herein, wherein A is phenyl substituted with two electron-withdrawing substituents. In certain embodiments, the invention relates to any one of the compounds described herein, wherein A is phenyl substituted in the 3-position with an electron-withdrawing substituent and in the 5-position with an electron-withdrawing substituent. In certain embodiments, the invention relates to any one of the compounds described herein, wherein A is phenyl substituted in the 2-position with an electron-withdrawing substituent and in the 6-position with an electron-withdrawing substituent.

In certain embodiments, the invention relates to any one of the compounds described herein, wherein the electron-withdrawing substituent is selected from the group consisting of —CHO, —C(O)R″, —C(O)OR″, —C(O)OH, —C(O)Cl, —CF$_3$, —CCl$_3$, —CN, SO$_3$H, —NO$_2$, and substituted or unsubstituted triazinyl; and R″ is alkyl, aryl, or aralkyl.

In certain embodiments, the invention relates to any one of the compounds described herein, wherein B is absent.

In certain embodiments, the invention relates to any one of the compounds described herein, wherein B is an optionally substituted heteroaromatic moiety. In certain embodiments, the invention relates to any one of the compounds described herein, wherein B is a substituted heteroaromatic moiety. In certain embodiments, the invention relates to any one of the compounds described herein, wherein B is an unsubstituted heteroaromatic moiety.

In certain embodiments, the invention relates to any one of the compounds described herein, wherein the B-ring is derived from an acridine, carbazole, carboline, cinnoline, furan, furazan, imidazole, indazole, indole, indolizine, isobenzofuran, isoindole, isoquinoline, isothiazole, isoxazole, naphthyridine, oxazole, phenanthridine, phenanthroline, phenazine, phthalazine, pteridine, purine, pyrazine, pyrazole, pyridazine, pyridine, pyrimidine, pyrrole, quinazoline, quinoline, quinoxaline, thiadiazole, thianthrene, thiophene, triazole, or trithiole. In certain embodiments, the invention relates to any one of the compounds described herein, wherein the B-ring is derived from an indole. In certain embodiments, the invention relates to any one of the compounds described herein, wherein the B-ring is

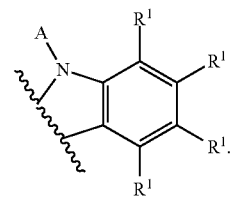

In certain embodiments, the invention relates to any one of the compounds described herein, wherein $R^1$ is hydrogen.

In certain embodiments, the invention relates to any one of the compounds described herein, wherein $R^1$ is alkyl. In certain embodiments, the invention relates to any one of the compounds described herein, wherein $R^1$ is methyl, ethyl, propyl, or butyl.

In certain embodiments, the invention relates to a compound of formula IIa', formula IIb', or formula IIc':

Formula IIa'

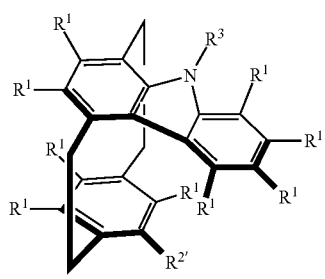

-continued

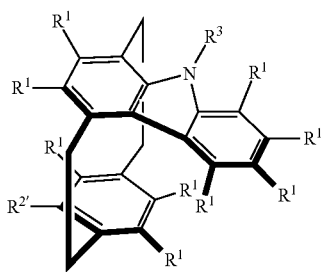

Formula IIb'

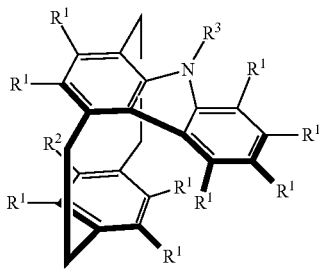

Formula IIc

Formula IIc' wherein
R¹ is, independently for each occurrence, hydrogen or alkyl;
R² is substituted or unsubstituted triazinyl or substituted or unsubstituted phenyl; and
R³ is hydrogen, alkyl, an optionally substituted aromatic moiety, or an optionally substituted heteroaromatic moiety.

wherein
R¹ is, independently for each occurrence, hydrogen or alkyl;
R²' is substituted or unsubstituted triazinyl, substituted or unsubstituted phenyl, substituted or unsubstituted pyridyl, substituted or unsubstituted pyrimidyl, or an electron-withdrawing group; and
R³ is hydrogen, alkyl, an optionally substituted aromatic moiety, or an optionally substituted heteroaromatic moiety.

In certain embodiments, the invention relates to a compound of formula IIa, formula IIb, or formula IIc:

Formula IIa

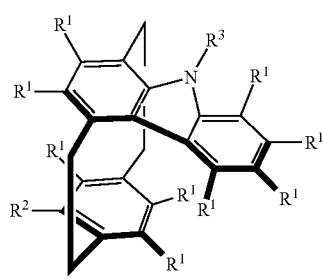

Formula IIb

In certain embodiments, the invention relates to any one of the compounds described herein, wherein R¹ is hydrogen.

In certain embodiments, the invention relates to any one of the compounds described herein, wherein R¹ is alkyl. In certain embodiments, the invention relates to any one of the compounds described herein, wherein R¹ is methyl, ethyl, propyl, or butyl.

In certain embodiments, the invention relates to any one of the compounds described herein, wherein R²' is substituted triazinyl. In certain embodiments, the invention relates to any one of the compounds described herein, wherein R²' is phenyl-substituted triazinyl. In certain embodiments, the invention relates to any one of the compounds described herein, wherein R²' is bisphenyl-substituted triazinyl.

In certain embodiments, the invention relates to any one of the compounds described herein, wherein R²' is unsubstituted triazinyl.

In certain embodiments, the invention relates to any one of the compounds described herein, wherein R²' is substituted phenyl. In certain embodiments, the invention relates to any one of the compounds described herein, wherein R²' is cyano-substituted phenyl or trifluoromethyl-substituted phenyl. In certain embodiments, the invention relates to any one of the compounds described herein, wherein R²' is dicyano-substituted phenyl or bistrifluoromethyl-substituted phenyl. In certain embodiments, the invention relates to any one of the compounds described herein, wherein R²' is 2,6-dicyanophenyl, 2,6-bistrifluoromethylphenyl, 3,5-dicyanophenyl, 3,5-bistrifluoromethylphenyl, or 4-cyanophenyl. In certain embodiments, the invention relates to any one of the compounds described herein, wherein R²' is 2,6-dicyanophenyl. In certain embodiments, the invention relates to any one of the compounds described herein, wherein R²' is 3,5-bistrifluoromethylphenyl.

In certain embodiments, the invention relates to any one of the compounds described herein, wherein R²' is unsubstituted phenyl.

In certain embodiments, the invention relates to any one of the compounds described herein, wherein R²' is substituted or unsubstituted pyridyl.

In certain embodiments, the invention relates to any one of the compounds described herein, wherein R²' is 4-pyridyl.

In certain embodiments, the invention relates to any one of the compounds described herein, wherein R²' is an electron-withdrawing group, such as 1,3,4-thiadiazolyl and 1,3,4-oxadiazolyl.

In certain embodiments, the invention relates to any one of the compounds described herein, wherein $R^{2'}$ is 2-pyrimidyl.

In certain embodiments, the invention relates to any one of the compounds described herein, wherein $R^2$ is substituted triazinyl. In certain embodiments, the invention relates to any one of the compounds described herein, wherein $R^2$ is phenyl-substituted triazinyl. In certain embodiments, the invention relates to any one of the compounds described herein, wherein $R^2$ is bisphenyl-substituted triazinyl.

In certain embodiments, the invention relates to any one of the compounds described herein, wherein $R^2$ is unsubstituted triazinyl.

In certain embodiments, the invention relates to any one of the compounds described herein, wherein $R^2$ is substituted phenyl. In certain embodiments, the invention relates to any one of the compounds described herein, wherein $R^2$ is cyano-substituted phenyl or trifluoromethyl-substituted phenyl. In certain embodiments, the invention relates to any one of the compounds described herein, wherein $R^2$ is dicyano-substituted phenyl or bistrifluoromethyl-substituted phenyl. In certain embodiments, the invention relates to any one of the compounds described herein, wherein $R^2$ is 2,6-dicyanophenyl, 2,6-bistrifluoromethylphenyl, 3,5-dicyanophenyl, 3,5-bistrifluoromethylphenyl, or 4-cyanophenyl. In certain embodiments, the invention relates to any one of the compounds described herein, wherein $R^2$ is 2,6-dicyanophenyl. In certain embodiments, the invention relates to any one of the compounds described herein, wherein $R^2$ is 3,5-bistrifluoromethylphenyl.

In certain embodiments, the invention relates to any one of the compounds described herein, wherein $R^2$ is unsubstituted phenyl.

In certain embodiments, the invention relates to any one of the compounds described herein, wherein $R^3$ is hydrogen.

In certain embodiments, the invention relates to any one of the compounds described herein, wherein $R^3$ is alkyl. In certain embodiments, the invention relates to any one of the compounds described herein, wherein $R^3$ is methyl, ethyl, propyl, or butyl.

In certain embodiments, the invention relates to any one of the compounds described herein, wherein $R^3$ is a substituted aromatic moiety.

In certain embodiments, the invention relates to any one of the compounds described herein, wherein $R^3$ is an unsubstituted aromatic moiety. In certain embodiments, the invention relates to any one of the compounds described herein, wherein $R^3$ is phenyl.

In certain embodiments, the invention relates to any one of the compounds described herein, wherein $R^3$ is a substituted heteroaromatic moiety.

In certain embodiments, the invention relates to any one of the compounds described herein, wherein $R^3$ is an unsubstituted heteroaromatic moiety.

In certain embodiments, the invention relates to any one of the compounds described herein, wherein $R^3$ is an aromatic moiety substituted with at least one electron-withdrawing substituent.

In certain embodiments, the invention relates to any one of the compounds described herein, wherein $R^3$ is phenyl substituted with at least one electron-withdrawing substituent.

In certain embodiments, the invention relates to any one of the compounds described herein, wherein $R^3$ is phenyl substituted with one electron-withdrawing substituent. In certain embodiments, the invention relates to any one of the compounds described herein, wherein $R^3$ is phenyl substituted with two electron-withdrawing substituents. In certain embodiments, the invention relates to any one of the compounds described herein, wherein $R^3$ is phenyl substituted in the 3-position with an electron-withdrawing substituent. In certain embodiments, the invention relates to any one of the compounds described herein, wherein $R^3$ is phenyl substituted in the 5-position with an electron-withdrawing substituent. In certain embodiments, the invention relates to any one of the compounds described herein, wherein $R^3$ is phenyl substituted in the 2-position with an electron-withdrawing substituent. In certain embodiments, the invention relates to any one of the compounds described herein, wherein $R^3$ is phenyl substituted in the 6-position with an electron-withdrawing substituent. In certain embodiments, the invention relates to any one of the compounds described herein, wherein $R^3$ is phenyl substituted in the 4-position with an electron-withdrawing substituent.

In certain embodiments, the invention relates to any one of the compounds described herein, wherein $R^3$ is phenyl substituted with two electron-withdrawing substituents. In certain embodiments, the invention relates to any one of the compounds described herein, wherein $R^3$ is phenyl substituted in the 3-position with an electron-withdrawing substituent and in the 5-position with an electron-withdrawing substituent. In certain embodiments, the invention relates to any one of the compounds described herein, wherein $R^3$ is phenyl substituted in the 2-position with an electron-withdrawing substituent and in the 6-position with an electron-withdrawing substituent.

In certain embodiments, the invention relates to any one of the compounds described herein, wherein the electron-withdrawing substituent is selected from the group consisting of —CHO, —C(O)R'', —C(O)OR'', —C(O)OH, —C(O)Cl, —CF$_3$, —CCl$_3$, —CN, SO$_3$H, —NO$_2$, and substituted or unsubstituted triazinyl; and R'' is alkyl, aryl, or aralkyl.

In certain embodiments, the invention relates to any one of the compounds described herein, wherein $R^3$ is an aromatic moiety substituted with at least one alkyl, aryl, or aralkyl substituent. In certain embodiments, the invention relates to any one of the compounds described herein, wherein $R^3$ is phenyl substituted with at least one alkyl, aryl, or aralkyl substituent.

In certain embodiments, the invention relates to any one of the compounds described herein, wherein $R^3$ is an aromatic moiety substituted with one alkyl, aryl, or aralkyl substituent. In certain embodiments, the invention relates to any one of the compounds described herein, wherein $R^3$ is phenyl substituted with one alkyl, aryl, or aralkyl substituent. In certain embodiments, the invention relates to any one of the compounds described herein, wherein $R^3$ is phenyl substituted in the 3-position with an alkyl, aryl, or aralkyl substituent. In certain embodiments, the invention relates to any one of the compounds described herein, wherein $R^3$ is phenyl substituted in the 5-position with an alkyl, aryl, or aralkyl substituent. In certain embodiments, the invention relates to any one of the compounds described herein, wherein $R^3$ is phenyl substituted in the 2-position with an alkyl, aryl, or aralkyl substituent. In certain embodiments, the invention relates to any one of the compounds described herein, wherein $R^3$ is phenyl substituted in the 6-position with an alkyl, aryl, or aralkyl substituent. In certain embodiments, the invention relates to any one of the compounds described herein, wherein $R^3$ is phenyl substituted in the 4-position with an alkyl, aryl, or aralkyl substituent.

In certain embodiments, the invention relates to any one of the compounds described herein, wherein $R^3$ is an aromatic moiety substituted with two alkyl, aryl, or aralkyl substituents. In certain embodiments, the invention relates to any one of the compounds described herein, wherein $R^3$ is phenyl substituted with two alkyl, aryl, or aralkyl substituents. In certain embodiments, the invention relates to any one of the compounds described herein, wherein $R^3$ is phenyl substituted in the 3-position with an alkyl, aryl, or aralkyl substituent and in the 5-position with an alkyl, aryl, or aralkyl substituent. In certain embodiments, the invention relates to any one of the compounds described herein, wherein $R^3$ is phenyl substituted in the 2-position with an alkyl, aryl, or aralkyl substituent and in the 6-position with an alkyl, aryl, or aralkyl substituent.

In certain embodiments, the invention relates to a compound of formula IIIa', formula IIIb', or formula IIIc':

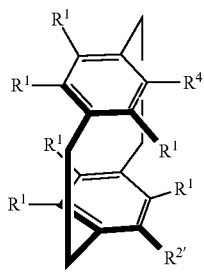

Formula IIIa'

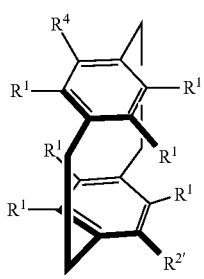

Formula IIIb'

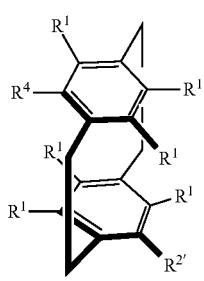

Formula IIIc' wherein $R^1$ is, independently for each occurrence, hydrogen or alkyl;

$R^{2'}$ is substituted or unsubstituted triazinyl, substituted or unsubstituted phenyl, substituted or unsubstituted pyridyl, substituted or unsubstituted pyrimidyl, or an electron-withdrawing group; and $R^4$ is hydrogen or an electron-donating group.

In certain embodiments, the invention relates to a compound of formula IIIa, formula IIIb, or formula IIIc:

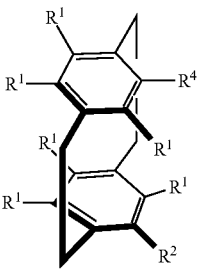

Formula IIIa

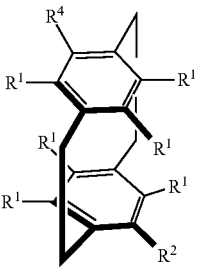

Formula IIIb

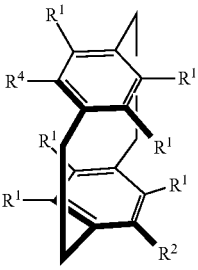

Formula IIIc wherein $R^1$ is, independently for each occurrence, hydrogen or alkyl;

$R^2$ is substituted or unsubstituted triazinyl or substituted or unsubstituted phenyl; and $R^4$ is hydrogen or an electron-donating group.

In certain embodiments, the invention relates to any one of the compounds described herein, wherein $R^1$ is hydrogen. In certain embodiments, the invention relates to any one of the compounds described herein, wherein $R^1$ is alkyl. In certain embodiments, the invention relates to any one of the compounds described herein, wherein $R^1$ is methyl, ethyl, propyl, or butyl.

In certain embodiments, the invention relates to any one of the compounds described herein, wherein $R^{2'}$ is substituted triazinyl. In certain embodiments, the invention relates to any one of the compounds described herein, wherein $R^{2'}$ is phenyl-substituted triazinyl. In certain embodiments, the invention relates to any one of the compounds described herein, wherein $R^{2'}$ is bisphenyl-substituted triazinyl.

In certain embodiments, the invention relates to any one of the compounds described herein, wherein $R^{2'}$ is unsubstituted triazinyl.

In certain embodiments, the invention relates to any one of the compounds described herein, wherein $R^{2'}$ is substituted phenyl. In certain embodiments, the invention relates to any one of the compounds described herein, wherein $R^{2'}$ is cyano-substituted phenyl or trifluoromethyl-substituted phenyl. In certain embodiments, the invention relates to any one of the compounds described herein, wherein $R^{2'}$ is dicyano-substituted phenyl or bistrifluoromethyl-substituted phenyl. In certain embodiments, the invention relates to any one of the compounds described herein, wherein $R^{2'}$ is 2,6-dicyanophenyl, 2,6-bistrifluoromethylphenyl, 3,5-dicyanophenyl, 3,5-bistrifluoromethylphenyl, or 4-cyanophenyl. In certain embodiments, the invention relates to any one of the compounds described herein, wherein $R^{2'}$ is 2,6-dicyanophenyl. In certain embodiments, the invention relates to any one of the compounds described herein, wherein $R^{2'}$ is 3,5-bistrifluoromethylphenyl.

In certain embodiments, the invention relates to any one of the compounds described herein, wherein $R^{2'}$ is unsubstituted phenyl.

In certain embodiments, the invention relates to any one of the compounds described herein, wherein $R^{2'}$ is substituted or unsubstituted pyridyl.

In certain embodiments, the invention relates to any one of the compounds described herein, wherein $R^{2'}$ is 4-pyridyl.

In certain embodiments, the invention relates to any one of the compounds described herein, wherein $R^{2'}$ is an electron-withdrawing group, such as 1,3,4-thiadiazolyl and 1,3,4-oxadiazolyl.

In certain embodiments, the invention relates to any one of the compounds described herein, wherein $R^{2'}$ is 2-pyrimidyl.

In certain embodiments, the invention relates to any one of the compounds described herein, wherein $R^2$ is substituted triazinyl. In certain embodiments, the invention relates to any one of the compounds described herein, wherein $R^2$ is phenyl-substituted triazinyl. In certain embodiments, the invention relates to any one of the compounds described herein, wherein $R^2$ is bisphenyl-substituted triazinyl.

In certain embodiments, the invention relates to any one of the compounds described herein, wherein $R^2$ is unsubstituted triazinyl.

In certain embodiments, the invention relates to any one of the compounds described herein, wherein $R^2$ is substituted phenyl. In certain embodiments, the invention relates to any one of the compounds described herein, wherein $R^2$ is cyano-substituted phenyl or trifluoromethyl-substituted phenyl. In certain embodiments, the invention relates to any one of the compounds described herein, wherein $R^2$ is dicyano-substituted phenyl or bistrifluoromethyl-substituted phenyl. In certain embodiments, the invention relates to any one of the compounds described herein, wherein $R^2$ is 2,6-dicyanophenyl, 2,6-bistrifluoromethylphenyl, 3,5-dicyanophenyl, 3,5-bistrifluoromethylphenyl, or 4-cyanophenyl. In certain embodiments, the invention relates to any one of the compounds described herein, wherein $R^2$ is 2,6-dicyanophenyl. In certain embodiments, the invention relates to any one of the compounds described herein, wherein $R^2$ is 3,5-bistrifluoromethylphenyl.

In certain embodiments, the invention relates to any one of the compounds described herein, wherein $R^2$ is unsubstituted phenyl.

In certain embodiments, the invention relates to any one of the compounds described herein, wherein $R^4$ is hydrogen.

In certain embodiments, the invention relates to any one of the compounds described herein, wherein $R^4$ is —NH$_2$, —NHR″, —N(R″)$_2$, —OH, —OR″, —NR″C(O)R″, —NHC(O)R″, or —OC(O)R″, wherein R″ is alkyl, aryl, or aralkyl, or, for instances where there are two R″, the two R″, taken together, form a ring. In certain embodiments, the invention relates to any one of the compounds described herein, wherein $R^4$ is —NH$_2$, —NHR″, —N(R″)$_2$, —OH, —OR″, —NR″C(O)R″, —NHC(O)R″, or —OC(O)R″, wherein R″ is alkyl, aryl, or aralkyl. In certain embodiments, the invention relates to any one of the compounds described herein, wherein $R^4$ is a nitrogen-containing heterocyclyl, including N-carbazolyl, N-(9,9-dialkyl-9,10-dihydroacridine), N-(9,9-diaryl-9,10-dihydroacridine), N-iminodibenzyl, N-iminostilbene, N-(9(10H)-acridanone), N-(10H-phenothiazine), N-(9H-3,9'-bicarbazole), N-(7,12-dihydro-5H-7,12-[1,2] benzenonaphtho[2,3-b]carbazole, and their derivatives (such as substituted N-carbazolyl and N-heterocyclic iminodibenzyl or iminostilbene).

In certain embodiments, the invention relates to any one of the compounds described herein, wherein $R^4$ is N-carbazolyl.

In certain embodiments, the invention relates to any one of the compounds described herein, wherein $R^4$ is —NH$_2$ or —N(alkyl)$_2$. In certain embodiments, the invention relates to any one of the compounds described herein, wherein $R^4$ is —NH$_2$ or —N(CH$_3$)$_2$.

In certain embodiments, the invention relates to any one of the compounds described herein, wherein $R^4$ is —N(aryl)$_2$. In certain embodiments, the invention relates to any one of the compounds described herein, wherein $R^4$ is —N(phenyl)$_2$.

In certain embodiments, the invention relates to any one of the compounds described herein, wherein $R^4$ is —O(alkyl). In certain embodiments, the invention relates to any one of the compounds described herein, wherein $R^4$ is —OCH$_3$.

In certain embodiments, the invention relates to a compound of formula IVa or formula IVb:

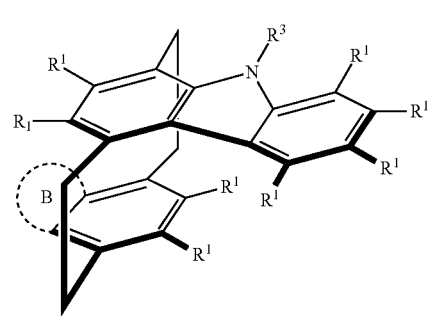

Formula IVa

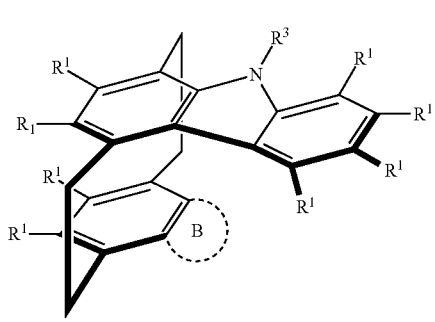

Formula IVb wherein
$R^1$ is, independently for each occurrence, hydrogen or alkyl;
B is absent or an optionally substituted heteroaromatic moiety; and
$R^3$ is hydrogen, alkyl, an optionally substituted aromatic moiety, or an optionally substituted heteroaromatic moiety.

In certain embodiments, the invention relates to any one of the compounds described herein, wherein $R^1$ is hydrogen.

In certain embodiments, the invention relates to any one of the compounds described herein, wherein $R^1$ is alkyl. In certain embodiments, the invention relates to any one of the compounds described herein, wherein $R^1$ is methyl, ethyl, propyl, or butyl.

In certain embodiments, the invention relates to any one of the compounds described herein, wherein $R^3$ is hydrogen.

In certain embodiments, the invention relates to any one of the compounds described herein, wherein $R^3$ is alkyl. In certain embodiments, the invention relates to any one of the compounds described herein, wherein $R^3$ is methyl, ethyl, propyl, or butyl.

In certain embodiments, the invention relates to any one of the compounds described herein, wherein $R^3$ is a substituted aromatic moiety.

In certain embodiments, the invention relates to any one of the compounds described herein, wherein $R^3$ is an unsubstituted aromatic moiety. In certain embodiments, the invention relates to any one of the compounds described herein, wherein $R^3$ is phenyl.

In certain embodiments, the invention relates to any one of the compounds described herein, wherein $R^3$ is a substituted heteroaromatic moiety.

In certain embodiments, the invention relates to any one of the compounds described herein, wherein $R^3$ is an unsubstituted heteroaromatic moiety.

In certain embodiments, the invention relates to any one of the compounds described herein, wherein $R^3$ is an aromatic moiety substituted with at least one electron-withdrawing substituent.

In certain embodiments, the invention relates to any one of the compounds described herein, wherein $R^3$ is phenyl substituted with at least one electron-withdrawing substituent.

In certain embodiments, the invention relates to any one of the compounds described herein, wherein $R^3$ is phenyl substituted with one electron-withdrawing substituent. In certain embodiments, the invention relates to any one of the compounds described herein, wherein $R^3$ is phenyl substituted with two electron-withdrawing substituents. In certain embodiments, the invention relates to any one of the compounds described herein, wherein $R^3$ is phenyl substituted in the 3-position with an electron-withdrawing substituent. In certain embodiments, the invention relates to any one of the compounds described herein, wherein $R^3$ is phenyl substituted in the 5-position with an electron-withdrawing substituent. In certain embodiments, the invention relates to any one of the compounds described herein, wherein $R^3$ is phenyl substituted in the 2-position with an electron-withdrawing substituent. In certain embodiments, the invention relates to any one of the compounds described herein, wherein $R^3$ is phenyl substituted in the 6-position with an electron-withdrawing substituent. In certain embodiments, the invention relates to any one of the compounds described herein, wherein $R^3$ is phenyl substituted in the 4-position with an electron-withdrawing substituent.

In certain embodiments, the invention relates to any one of the compounds described herein, wherein $R^3$ is phenyl substituted with two electron-withdrawing substituents. In certain embodiments, the invention relates to any one of the compounds described herein, wherein $R^3$ is phenyl substituted in the 3-position with an electron-withdrawing substituent and in the 5-position with an electron-withdrawing substituent. In certain embodiments, the invention relates to any one of the compounds described herein, wherein $R^3$ is phenyl substituted in the 2-position with an electron-withdrawing substituent and in the 6-position with an electron-withdrawing substituent.

In certain embodiments, the invention relates to any one of the compounds described herein, wherein the electron-withdrawing substituent is selected from the group consisting of —CHO, —C(O)R'', —C(O)OR'', —C(O)OH, —C(O)Cl, —CF$_3$, —CCl$_3$, —CN, SO$_3$H, —NO$_2$, and substituted or unsubstituted triazinyl; and R'' is alkyl, aryl, or aralkyl.

In certain embodiments, the invention relates to any one of the compounds described herein, wherein $R^3$ is an aromatic moiety substituted with at least one alkyl, aryl, or aralkyl substituent. In certain embodiments, the invention relates to any one of the compounds described herein, wherein $R^3$ is phenyl substituted with at least one alkyl, aryl, or aralkyl substituent.

In certain embodiments, the invention relates to any one of the compounds described herein, wherein $R^3$ is an aromatic moiety substituted with one alkyl, aryl, or aralkyl substituent. In certain embodiments, the invention relates to any one of the compounds described herein, wherein $R^3$ is phenyl substituted with one alkyl, aryl, or aralkyl substituent. In certain embodiments, the invention relates to any one of the compounds described herein, wherein $R^3$ is phenyl substituted in the 3-position with an alkyl, aryl, or aralkyl substituent. In certain embodiments, the invention relates to any one of the compounds described herein, wherein $R^3$ is phenyl substituted in the 5-position with an alkyl, aryl, or aralkyl substituent. In certain embodiments, the invention relates to any one of the compounds described herein, wherein $R^3$ is phenyl substituted in the 2-position with an alkyl, aryl, or aralkyl substituent. In certain embodiments, the invention relates to any one of the compounds described herein, wherein $R^3$ is phenyl substituted in the 6-position with an alkyl, aryl, or aralkyl substituent. In certain embodiments, the invention relates to any one of the compounds described herein, wherein $R^3$ is phenyl substituted in the 4-position with an alkyl, aryl, or aralkyl substituent.

In certain embodiments, the invention relates to any one of the compounds described herein, wherein $R^3$ is an aromatic moiety substituted with two alkyl, aryl, or aralkyl substituents. In certain embodiments, the invention relates to any one of the compounds described herein, wherein $R^3$ is phenyl substituted with two alkyl, aryl, or aralkyl substituents. In certain embodiments, the invention relates to any one of the compounds described herein, wherein $R^3$ is phenyl substituted in the 3-position with an alkyl, aryl, or aralkyl substituent and in the 5-position with an alkyl, aryl, or aralkyl substituent. In certain embodiments, the invention relates to any one of the compounds described herein, wherein $R^3$ is phenyl substituted in the 2-position with an alkyl, aryl, or aralkyl substituent and in the 6-position with an alkyl, aryl, or aralkyl substituent.

In certain embodiments, the invention relates to any one of the compounds described herein, wherein B is absent.

In certain embodiments, the invention relates to any one of the compounds described herein, wherein B is an optionally substituted heteroaromatic moiety. In certain embodiments, the invention relates to any one of the compounds described herein, wherein B is a substituted heteroaromatic moiety. In certain embodiments, the invention relates to any one of the compounds described herein, wherein B is an unsubstituted heteroaromatic moiety.

In certain embodiments, the invention relates to any one of the compounds described herein, wherein the B-ring is derived from an acridine, carbazole, carboline, cinnoline, furan, furazan, imidazole, indazole, indole, indolizine, isobenzofuran, isoindole, isoquinoline, isothiazole, isoxazole, naphthyridine, oxazole, phenanthridine, phenanthroline, phenazine, phthalazine, pteridine, purine, pyrazine, pyrazole, pyridazine, pyridine, pyrimidine, pyrrole, quinazoline, quinoline, quinoxaline, thiadiazole, thianthrene, thiophene, triazole, or trithiole.

In certain embodiments, the invention relates to any one of the compounds described herein, wherein the B-ring is derived from a pyridine, quinoline, thiadiazole, triazole, or trithiole.

In certain embodiments, the invention relates to a compound of formula Va or formula Vb:

Formula Va

Formula Vb wherein
$R^1$ is, independently for each occurrence, hydrogen or alkyl;
B is absent or an optionally substituted heteroaromatic moiety;
X is O, S, or $NR^3$; and
$R^3$ is hydrogen, alkyl, an optionally substituted aromatic moiety, or an optionally substituted heteroaromatic moiety.

In certain embodiments, the invention relates to any one of the compounds described herein, wherein $R^1$ is hydrogen.

In certain embodiments, the invention relates to any one of the compounds described herein, wherein $R^1$ is alkyl. In certain embodiments, the invention relates to any one of the compounds described herein, wherein $R^1$ is methyl, ethyl, propyl, or butyl.

In certain embodiments, the invention relates to any one of the compounds described herein, wherein X is O.

In certain embodiments, the invention relates to any one of the compounds described herein, wherein X is S.

In certain embodiments, the invention relates to any one of the compounds described herein, wherein X is $NR^3$.

In certain embodiments, the invention relates to any one of the compounds described herein, wherein $R^3$ is hydrogen.

In certain embodiments, the invention relates to any one of the compounds described herein, wherein $R^3$ is alkyl. In certain embodiments, the invention relates to any one of the compounds described herein, wherein $R^3$ is methyl, ethyl, propyl, or butyl.

In certain embodiments, the invention relates to any one of the compounds described herein, wherein $R^3$ is a substituted aromatic moiety.

In certain embodiments, the invention relates to any one of the compounds described herein, wherein $R^3$ is an unsubstituted aromatic moiety. In certain embodiments, the invention relates to any one of the compounds described herein, wherein $R^3$ is phenyl.

In certain embodiments, the invention relates to any one of the compounds described herein, wherein $R^3$ is a substituted heteroaromatic moiety.

In certain embodiments, the invention relates to any one of the compounds described herein, wherein $R^3$ is an unsubstituted heteroaromatic moiety.

In certain embodiments, the invention relates to any one of the compounds described herein, wherein $R^3$ is an aromatic moiety substituted with at least one electron-withdrawing substituent.

In certain embodiments, the invention relates to any one of the compounds described herein, wherein $R^3$ is phenyl substituted with at least one electron-withdrawing substituent.

In certain embodiments, the invention relates to any one of the compounds described herein, wherein $R^3$ is phenyl substituted with one electron-withdrawing substituent. In certain embodiments, the invention relates to any one of the compounds described herein, wherein $R^3$ is phenyl substituted with two electron-withdrawing substituents. In certain embodiments, the invention relates to any one of the compounds described herein, wherein $R^3$ is phenyl substituted in the 3-position with an electron-withdrawing substituent. In certain embodiments, the invention relates to any one of the compounds described herein, wherein $R^3$ is phenyl substituted in the 5-position with an electron-withdrawing substituent. In certain embodiments, the invention relates to any one of the compounds described herein, wherein $R^3$ is phenyl substituted in the 2-position with an electron-withdrawing substituent. In certain embodiments, the invention relates to any one of the compounds described herein, wherein $R^3$ is phenyl substituted in the 6-position with an electron-withdrawing substituent. In certain embodiments, the invention relates to any one of the compounds described herein, wherein $R^3$ is phenyl substituted in the 4-position with an electron-withdrawing substituent.

In certain embodiments, the invention relates to any one of the compounds described herein, wherein $R^3$ is phenyl substituted with two electron-withdrawing substituents. In certain embodiments, the invention relates to any one of the compounds described herein, wherein $R^3$ is phenyl substituted in the 3-position with an electron-withdrawing substituent and in the 5-position with an electron-withdrawing substituent. In certain embodiments, the invention relates to any one of the compounds described herein, wherein $R^3$ is phenyl substituted in the 2-position with an electron-withdrawing substituent and in the 6-position with an electron-withdrawing substituent.

In certain embodiments, the invention relates to any one of the compounds described herein, wherein the electron-withdrawing substituent is selected from the group consisting of —CHO, —C(O)R″, —C(O)OR″, —C(O)OH, —C(O)Cl, —CF$_3$, —CCl$_3$, —CN, SO$_3$H, —NO$_2$, and substituted or unsubstituted triazinyl; and R″ is alkyl, aryl, or aralkyl.

In certain embodiments, the invention relates to any one of the compounds described herein, wherein $R^3$ is an aromatic moiety substituted with at least one alkyl, aryl, or aralkyl substituent. In certain embodiments, the invention relates to any one of the compounds described herein, wherein $R^3$ is phenyl substituted with at least one alkyl, aryl, or aralkyl substituent.

In certain embodiments, the invention relates to any one of the compounds described herein, wherein $R^3$ is an aromatic moiety substituted with one alkyl, aryl, or aralkyl substituent. In certain embodiments, the invention relates to any one of the compounds described herein, wherein $R^3$ is phenyl substituted with one alkyl, aryl, or aralkyl substituent. In certain embodiments, the invention relates to any one of the compounds described herein, wherein $R^3$ is phenyl substituted in the 3-position with an alkyl, aryl, or aralkyl substituent. In certain embodiments, the invention relates to any one of the compounds described herein, wherein $R^3$ is phenyl substituted in the 5-position with an alkyl, aryl, or aralkyl substituent. In certain embodiments, the invention relates to any one of the compounds described herein, wherein $R^3$ is phenyl substituted in the 2-position with an alkyl, aryl, or aralkyl substituent. In certain embodiments, the invention relates to any one of the compounds described herein, wherein $R^3$ is phenyl substituted in the 6-position with an alkyl, aryl, or aralkyl substituent. In certain embodiments, the invention relates to any one of the compounds described herein, wherein $R^3$ is phenyl substituted in the 4-position with an alkyl, aryl, or aralkyl substituent.

In certain embodiments, the invention relates to any one of the compounds described herein, wherein $R^3$ is an aromatic moiety substituted with two alkyl, aryl, or aralkyl substituents. In certain embodiments, the invention relates to any one of the compounds described herein, wherein $R^3$ is phenyl substituted with two alkyl, aryl, or aralkyl substituents. In certain embodiments, the invention relates to any one of the compounds described herein, wherein $R^3$ is phenyl substituted in the 3-position with an alkyl, aryl, or aralkyl substituent and in the 5-position with an alkyl, aryl, or aralkyl substituent. In certain embodiments, the invention relates to any one of the compounds described herein, wherein $R^3$ is phenyl substituted in the 2-position with an alkyl, aryl, or aralkyl substituent and in the 6-position with an alkyl, aryl, or aralkyl substituent.

In certain embodiments, the invention relates to any one of the compounds described herein, wherein B is absent.

In certain embodiments, the invention relates to any one of the compounds described herein, wherein B is an optionally substituted heteroaromatic moiety. In certain embodiments, the invention relates to any one of the compounds described herein, wherein B is a substituted heteroaromatic moiety. In certain embodiments, the invention relates to any one of the compounds described herein, wherein B is an unsubstituted heteroaromatic moiety.

In certain embodiments, the invention relates to any one of the compounds described herein, wherein the B-ring is derived from an acridine, carbazole, carboline, cinnoline, furan, furazan, imidazole, indazole, indole, indolizine, isobenzofuran, isoindole, isoquinoline, isothiazole, isoxazole, naphthyridine, oxazole, phenanthridine, phenanthroline, phenazine, phthalazine, pteridine, purine, pyrazine, pyrazole, pyridazine, pyridine, pyrimidine, pyrrole, quinazoline, quinoline, quinoxaline, thiadiazole, thianthrene, thiophene, triazole, or trithiole.

In certain embodiments, the invention relates to any one of the compounds described herein, wherein the B-ring is derived from a pyridine, quinoline, thiadiazole, triazole, or trithiole.

In certain embodiments, the invention relates to any one of the compounds described herein, in the form of a thin film, a thick film, or a crystal.

In certain embodiments, the invention relates to any one of the compounds described herein, wherein the compound is depicted in the Figures or in the Examples.

Exemplary Polymers

In certain embodiments, the invention relates to a polymer comprising a repeat unit of formula VIa or formula VIb:

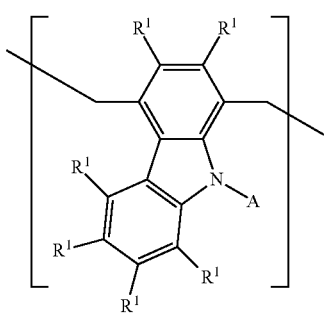

Formula VIa

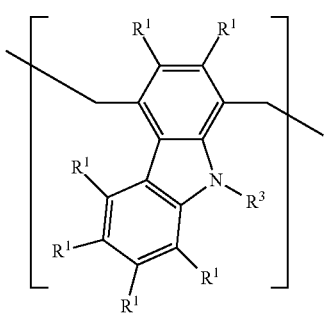

Formula VIb wherein, independently for each occurrence,

A is an aromatic moiety substituted with at least one electron-withdrawing substituent or a heteroaromatic moiety substituted with at least one electron-withdrawing substituent;

$R^1$ is, independently for each occurrence, hydrogen or alkyl; and $R^3$ is hydrogen, alkyl, an optionally substituted aromatic moiety, or an optionally substituted heteroaromatic moiety.

In certain embodiments, the invention relates to any one of the polymers described herein, wherein A is an aromatic moiety substituted with at least one electron-withdrawing substituent.

In certain embodiments, the invention relates to any one of the polymers described herein, wherein A is a heteroaromatic moiety substituted with at least one electron-withdrawing substituent.

In certain embodiments, the invention relates to any one of the polymers described herein, wherein A is phenyl substituted with at least one electron-withdrawing substituent.

In certain embodiments, the invention relates to any one of the polymers described herein, wherein A is phenyl substituted with one electron-withdrawing substituent. In certain embodiments, the invention relates to any one of the polymers described herein, wherein A is phenyl substituted with two electron-withdrawing substituents. In certain embodiments, the invention relates to any one of the polymers described herein, wherein A is phenyl substituted in the 3-position with an electron-withdrawing substituent. In certain embodiments, the invention relates to any one of the polymers described herein, wherein A is phenyl substituted in the 5-position with an electron-withdrawing substituent. In certain embodiments, the invention relates to any one of the polymers described herein, wherein A is phenyl substituted in the 2-position with an electron-withdrawing substituent. In certain embodiments, the invention relates to any one of the polymers described herein, wherein A is phenyl substituted in the 6-position with an electron-withdrawing substituent. In certain embodiments, the invention relates to any one of the polymers described herein, wherein A is phenyl substituted in the 4-position with an electron-withdrawing substituent.

In certain embodiments, the invention relates to any one of the polymers described herein, wherein A is phenyl substituted with two electron-withdrawing substituents. In certain embodiments, the invention relates to any one of the polymers described herein, wherein A is phenyl substituted in the 3-position with an electron-withdrawing substituent and in the 5-position with an electron-withdrawing substituent. In certain embodiments, the invention relates to any one of the polymers described herein, wherein A is phenyl substituted in the 2-position with an electron-withdrawing substituent and in the 6-position with an electron-withdrawing substituent.

In certain embodiments, the invention relates to any one of the polymers described herein, wherein the electron-withdrawing substituent is selected from the group consisting of —CHO, —C(O)R″, —C(O)OR″, —C(O)OH, —C(O)Cl, —CF$_3$, —CCl$_3$, —CN, SO$_3$H, —NO$_2$, and substituted or unsubstituted triazinyl; and R″ is alkyl, aryl, or aralkyl.

In certain embodiments, the invention relates to any one of the polymers described herein, wherein $R^1$ is hydrogen.

In certain embodiments, the invention relates to any one of the polymers described herein, wherein $R^1$ is alkyl. In certain embodiments, the invention relates to any one of the polymers described herein, wherein $R^1$ is methyl, ethyl, propyl, or butyl.

In certain embodiments, the invention relates to any one of the polymers described herein, wherein $R^3$ is hydrogen.

In certain embodiments, the invention relates to any one of the polymers described herein, wherein $R^3$ is alkyl. In certain embodiments, the invention relates to any one of the polymers described herein, wherein $R^3$ is methyl, ethyl, propyl, or butyl.

In certain embodiments, the invention relates to any one of the polymers described herein, wherein $R^3$ is a substituted aromatic moiety.

In certain embodiments, the invention relates to any one of the polymers described herein, wherein $R^3$ is an unsubstituted aromatic moiety. In certain embodiments, the invention relates to any one of the polymers described herein, wherein $R^3$ is phenyl.

In certain embodiments, the invention relates to any one of the polymers described herein, wherein $R^3$ is a substituted heteroaromatic moiety.

In certain embodiments, the invention relates to any one of the polymers described herein, wherein $R^3$ is an unsubstituted heteroaromatic moiety.

In certain embodiments, the invention relates to any one of the polymers described herein, wherein $R^3$ is an aromatic moiety substituted with at least one electron-withdrawing substituent.

In certain embodiments, the invention relates to any one of the polymers described herein, wherein $R^3$ is phenyl substituted with at least one electron-withdrawing substituent.

In certain embodiments, the invention relates to any one of the polymers described herein, wherein $R^3$ is phenyl substituted with one electron-withdrawing substituent. In certain embodiments, the invention relates to any one of the polymers described herein, wherein $R^3$ is phenyl substituted with two electron-withdrawing substituents. In certain embodiments, the invention relates to any one of the polymers described herein, wherein $R^3$ is phenyl substituted in the 3-position with an electron-withdrawing substituent. In certain embodiments, the invention relates to any one of the polymers described herein, wherein $R^3$ is phenyl substituted in the 5-position with an electron-withdrawing substituent. In certain embodiments, the invention relates to any one of the polymers described herein, wherein $R^3$ is phenyl substituted in the 2-position with an electron-withdrawing substituent. In certain embodiments, the invention relates to any one of the polymers described herein, wherein $R^3$ is phenyl substituted in the 6-position with an electron-withdrawing substituent. In certain embodiments, the invention relates to any one of the polymers described herein, wherein $R^3$ is phenyl substituted in the 4-position with an electron-withdrawing substituent.

In certain embodiments, the invention relates to any one of the polymers described herein, wherein $R^3$ is phenyl substituted with two electron-withdrawing substituents. In certain embodiments, the invention relates to any one of the polymers described herein, wherein $R^3$ is phenyl substituted in the 3-position with an electron-withdrawing substituent and in the 5-position with an electron-withdrawing substituent. In certain embodiments, the invention relates to any one of the polymers described herein, wherein $R^3$ is phenyl substituted in the 2-position with an electron-withdrawing substituent and in the 6-position with an electron-withdrawing substituent.

In certain embodiments, the invention relates to any one of the polymers described herein, wherein the electron-withdrawing substituent is selected from the group consisting of —CHO, —C(O)R″, —C(O)OR″, —C(O)OH, —C(O)Cl, —CF$_3$, —CCl$_3$, —CN, SO$_3$H, —NO$_2$, and substituted or unsubstituted triazinyl; and R″ is alkyl, aryl, or aralkyl.

In certain embodiments, the invention relates to any one of the polymers described herein, wherein $R^3$ is an aromatic moiety substituted with at least one alkyl, aryl, or aralkyl substituent. In certain embodiments, the invention relates to any one of the polymers described herein, wherein $R^3$ is phenyl substituted with at least one alkyl, aryl, or aralkyl substituent.

In certain embodiments, the invention relates to any one of the polymers described herein, wherein $R^3$ is an aromatic moiety substituted with one alkyl, aryl, or aralkyl substituent. In certain embodiments, the invention relates to any one of the polymers described herein, wherein $R^3$ is phenyl substituted with one alkyl, aryl, or aralkyl substituent. In certain embodiments, the invention relates to any one of the polymers described herein, wherein $R^3$ is phenyl substituted in the 3-position with an alkyl, aryl, or aralkyl substituent. In certain embodiments, the invention relates to any one of the polymers described herein, wherein $R^3$ is phenyl substituted in the 5-position with an alkyl, aryl, or aralkyl substituent. In certain embodiments, the invention relates to any one of the polymers described herein, wherein $R^3$ is phenyl substituted in the 2-position with an alkyl, aryl, or aralkyl substituent. In certain embodiments, the invention relates to any one of the polymers described herein, wherein $R^3$ is phenyl substituted in the 6-position with an alkyl, aryl, or aralkyl substituent. In certain embodiments, the invention relates to any one of the polymers described herein, wherein $R^3$ is phenyl substituted in the 4-position with an alkyl, aryl, or aralkyl substituent.

In certain embodiments, the invention relates to any one of the polymers described herein, wherein $R^3$ is an aromatic moiety substituted with two alkyl, aryl, or aralkyl substituents. In certain embodiments, the invention relates to any one of the polymers described herein, wherein $R^3$ is phenyl substituted with two alkyl, aryl, or aralkyl substituents. In certain embodiments, the invention relates to any one of the polymers described herein, wherein $R^3$ is phenyl substituted in the 3-position with an alkyl, aryl, or aralkyl substituent and in the 5-position with an alkyl, aryl, or aralkyl substituent. In certain embodiments, the invention relates to any one of the polymers described herein, wherein $R^3$ is phenyl substituted in the 2-position with an alkyl, aryl, or aralkyl substituent and in the 6-position with an alkyl, aryl, or aralkyl substituent.

In certain embodiments, the invention relates to any one of the polymers described herein, wherein the polymer is depicted in the Examples.

Exemplary Electronic Devices

Figure 4A:
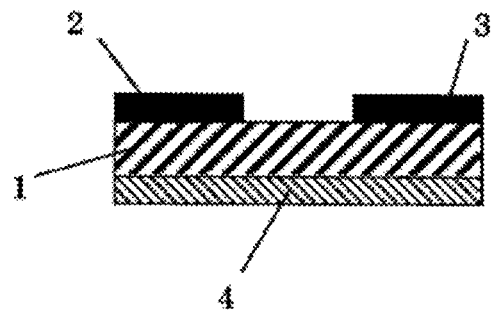
FIG. 4A depicts a schematic structural diagram showing an electronic device of the invention.
Figure 4B:
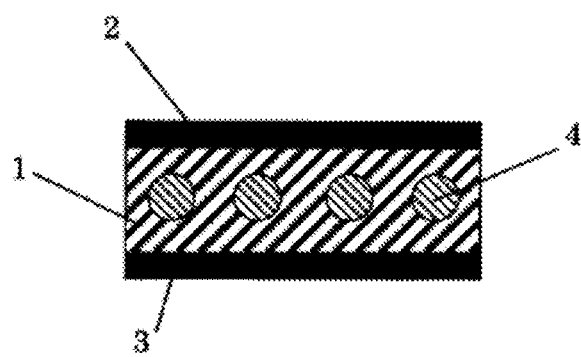
FIG. 4B depicts a schematic structural diagram showing an electronic device of the invention.

In certain embodiments, the invention relates to an electronic device, such as an OLED, comprising an anode (2), a cathode (3), and an emissive layer (1), wherein the emissive layer is disposed between the anode and the cathode; and the emissive layer comprises any of the compounds described herein or any one of the polymers described herein. See, for example, FIG. 4.

In certain embodiments, the invention relates to any one of the electronic devices described herein, wherein the emissive layer further comprises an emissive dopant.

In certain embodiments, the invention relates to any one of the electronic devices described herein, wherein the compound or the polymer is used directly as the emissive layer, or forms an emissive host material in a case where the emissive layer comprises a host material plus an emissive dopant.

In certain embodiments, the invention relates to any one of the electronic devices described herein, wherein the emissive dopant is a hole transport material. In certain embodiments, the hole transport material is, for example, poly(9-vinyl carbazole), tris-[(N,N-diaryl)amino]triphenylamine, for example 4,4',4"-tris[(N-(1-naphthyl)-N-phenylaminotriphenyl-amine] (1-TNATA) and its derivatives, 4,4',4"-tris[(N-(2-naphthyl)-N-phenylamino)-triphenylamine] (2-TNATA) or 4,4',4"-tris[(N-(3-methylphenyl)-N-phenylamino)-triphenylamine] (m-TDATA) and its derivatives, 4,4',4"-tris (carbazol-9-yl)triphenylamines; N,N,N',N'-tetraarylbenzidine, in particular N,N,N',N'-tetraphenylbenzidine and its derivatives, N,N'-bis(naphthalen-1-yl)-N,N'-diphenylbenzidine, N,N'-bis(naphthalen-2-yl)-N,N'-diphenylbenzidine, 4,4'-bis(carbazol-9-yl)biphenyl (CBP) and its derivatives and its analogues substituted by heteroatoms (for example, thienyl, selenyl, furanyl derivatives); 4,4'-bis(2,2'-diphenylvinyl)-1,1'-biphenyl (DPVBi); triarylamines and their derivatives, 4,4'-bis(N,N-diarylamino)alkylterphenyls, N,N'-dimethylquinacridone and its derivatives, 1,1-bis(4-bis (4-methyl-phenyl)-aminophenyl)-cyclohexane (TAPC), and N,N,N',N'-tetraaryldiaminofluorene and their derivatives.

In certain embodiments, the invention relates to any one of the electronic devices described herein, wherein the emissive dopant is an electron transport material. In certain embodiments, the electron transport material is, for example, 4,7-diphenyl-1,10-phenanthroline (Bphen) and derivatives thereof, especially 2,9-dimethyl-4,7-diphenyl-1,10-phenanthroline (BCP), 2,5-diaryloxadiazole and their derivatives, such as 2-(4-tert-butylphenyl)-5-(4-biphenyl)-oxadiazole (PBD), oligo(benzoxadiazol-2-yl)arenes and their derivatives, such as bis-2,5-(5-tert-butyl-benzoxadizol-2-yl)-thiophene (BBOT), 1,3-bis[5-(aryl)-1,3,4-oxadiazol-2-yl]benzene and their derivatives, such as 1,3-bis[5-(4-tert-butylphenyl)-1,3,4-oxadiazol-2-yl]benzene (OXD-7), 2,5-diaryltriazole and their derivatives, such as 2-(4-tert-butylphenyl)-5-(4-biphenyl)-triazole (TAZ).

In certain embodiments, the invention relates to any one of the electronic devices described herein, further comprising a gate electrode (4). In certain embodiments, the gate electrode is in contact with the cathode and the anode.

In certain embodiments, the invention relates to any one of the electronic devices described herein, further comprising an insulating film (5). In certain embodiments, the insulating film may be formed between the gate electrode 4 and the emissive layer 1.

In certain embodiments, the invention relates to any one of the electronic devices described herein, wherein the insulating film is formed using various insulating film materials. Examples of the insulating materials include inorganic insulating film materials such as silicon oxide, silicon nitride, aluminum oxide, aluminum nitride, titanium oxide, tantalum oxide, tin oxide, vanadium oxide, barium strontium titanate, barium zirconate titanate, lead zirconate titanate, lanthanum lead titanate, strontium titanate, barium titanate, magnesium barium fluoride, bismuth tantalate niobate, and yttrium trioxide.

Examples thereof also include organic polymer insulating film material such as polyimide, polyvinyl alcohol, polyvinyl phenol, polyester, polyethylene, polyphenylene sulfide, polystyrene, polymethacrylate, unsubstituted or halogen-substituted polyparaxylylene, polyacrylonitrile, and cyanoethyl pullulan.

Moreover, two or more insulating film materials may be used in combination. Among the aforementioned insulating film materials, preferable materials are ones having high dielectric constant and low conductivity, but not limited to the specific materials.

Examples of a method for forming the insulating film include: dry processes, such as CVD, plasma CVD, plasma polymerization, and deposition; and wet processes, such as spray-coating, spin-coating, dip-coating, inkjet-printing, casting, blade-coating, and bar-coating.

In certain embodiments, the invention relates to any one of the electronic devices described herein, further comprising an organic thin film between the emissive layer and the insulating film for the purpose of improving the adhesion between the emissive layer and the insulating film, and reducing the driving voltage and leak current, etc.

In certain embodiments, the organic thin film does not chemically affect the emissive layer. For example, an organic molecular film or polymer thin film can be used as the organic thin film.

Examples of the organic thin film include a film formed of a coupling agent, such as octadecyltrichlorosilane, and hexamethyldisilazane.

The organic thin film may be formed of any one of the aforementioned polymer insulating film materials, and can also function as an insulating film.

In certain embodiments, the invention relates to any one of the electronic devices described herein, wherein an electric current running through the portion of the emissive layer 1 between the anode 2 and the cathode 3 is controlled by adjusting the voltage applied to the gate electrode 4.

In certain embodiments, the invention relates to any one of the electronic devices described herein, wherein the state of the applied voltage to the gate electrode can largely influence the amount of the current running between the anode and the cathode.

In certain embodiments, the invention relates to any one of the electronic devices described herein, wherein the gate electrode and the anode are suitably selected depending on the intended purpose without any restriction, provided that they are formed of a conductive material. Examples of the conductive material include: metals such as platinum, gold, silver, nickel, chromium, cupper, iron, tin, antimony, lead, tantalum, indium, aluminum, zinc, and magnesium; alloys such as alloys of the aforementioned metals; conductive metal oxides such as indium tin oxide; and inorganic or organic semiconductor having the conductivity improved by doping or the like, where examples of inorganic or organic materials used for such inorganic or organic semiconductor include silicon monocrystal, polysilicon, amorphous silicon, germanium, graphite, polyacetylene, polyparaphenylene, polythiophene, polypyrrole, polyaniline, polythienylenevinylene, polyparaphenylenevinylene and a complex compound of polyethylenedioxythiophene and polystyrene sulfonic add.

In certain embodiments, the invention relates to any one of the electronic devices described herein, wherein the anode and the cathode each have low electric resistance at the contact plane thereof with the emissive layer.

General procedures for an OLED fabrication are as follows:
1) Obtain clean ITO substrates coated with a patterned layer.
2) Treat the substrates with $O_2$ plasma for 1-5 minutes.
3) Place the substrates in a thermal evaporator and pump down the pressure below $6 \times 10^{-6}$ torr.
4) Evaporate organic and metallic layers onto the substrates.
   a. A hole transport layer is evaporated with a thickness of ~200 Å.
   b. Usually the emissive layer is evaporated with a host and a dopant. With the shutter closed to prevent premature deposition, the evaporation of the dopant is stabilized at a rate around 0.03 Å/s. Then, the evaporation of the host is stabilized at a rate around 1-3 Å/s, giving a doping concentration of about 1-3%. The shutter is then opened, and deposition is monitored by a quartz crystal monitor. Usually 100-400 Å of the emissive layer is deposited.
   c. The electron transporting material is evaporated at a rate of approximately 1-3 Å/s to form a layer that is usually 200-400 Å thick.
   d. A mask is placed next to the substrates to define where metallic electrodes are to be evaporated.
   e. About 120 Å of a Li—Al alloy is evaporated to improve electron injection into the device.
   f. 1500 Å of Al is deposited, and the evaporator is allowed to cool.
5) Test the devices for luminance, color, and current-voltage characteristics.

Exemplary Methods

In certain embodiments, the invention relates to a method of producing visible light comprising applying a charge to any one of the electronic devices described herein.

In certain embodiments, the invention relates to any one of the methods described herein, wherein the visible light has a wavelength of from about 400 nm to about 500 nm. In certain embodiments, the invention relates to any one of the methods described herein, wherein the visible light has a wavelength of about 400 nm, about 410 nm, about 420 nm, about 430 nm, about 440 nm, about 450 nm, about 460 nm, about 470 nm, about 480 nm, about 490 nm, or about 500 nm. In certain embodiments, the invention relates to any one of the methods described herein, wherein the visible light has a wavelength of about 450 nm.

In certain embodiments, the invention relates to any one of the methods described herein, wherein the external quantum efficiency of the device or the method is at least about 5%, about 10%, or about 15%.

In certain embodiments, the invention relates to any one of the methods described herein, wherein the emission decay time of the device or the method is from about 0.5 µs to about 1.5 µs. In certain embodiments, the invention relates to any one of the methods described herein, wherein the emission decay time of the device or the method is about 0.5 µs, about 0.6 µs, about 0.7 µs, about 0.8 µs, about 0.9 µs, about 1.0 µs, about 1.1 µs, about 1.2 µs, about 1.3 µs, about 1.4 µs, or about 1.5 µs. In certain embodiments, the invention relates to any one of the methods described herein, wherein the emission decay time of the device or the method is about 1.0 µs.

In certain embodiments, the invention relates to any one of the methods described herein, wherein the brightness of the visible light is greater than about 500 cd m$^{-2}$, about 600 cd m$^{-2}$, about 700 cd m$^{-2}$, about 800 cd m$^{-2}$, about 900 cd m$^{-2}$, about 1000 cd m$^{-2}$, about 1100 cd m$^{-2}$, about 1200 cd m$^{-2}$, about 1300 cd m$^{-2}$, about 1400 cd m$^{-2}$, or about 1500 cd m$^{-2}$. In certain embodiments, the invention relates to any one of the methods described herein, wherein the brightness of the visible light is greater than about 1000 cd m$^{-2}$.

In certain embodiments, the invention relates to any one of the methods described herein, wherein visible light is still produced after application of the charge for a period of time (lifetime). In certain embodiments, the invention relates to any one of the methods described herein, wherein period of time is at least about 5,000 h, about 6,000 h, about 7,000 h, about 8,000 h, about 9,000 h about 10,000 h, about 11,000 h, about 12,000 h, about 13,000 h, about 14,000 h, or about 15,000 h. In certain embodiments, the invention relates to any one of the methods described herein, wherein period of time is at least about 10,000 h. In certain embodiments, the invention relates to any one of the methods described herein, wherein period of time is at least about 5,000 h, about 6,000 h, about 7,000 h, about 8,000 h, about 9,000 h, about 10,000 h. about 11,000 h, about 12,000 h, about 13,000 h, about 14,000 h, or about 15,000 h under at least about 100 cd m$^{-2}$. In certain embodiments, the invention relates to any one of the methods described herein, wherein period of time is at least about 10,000 h under at least about 100 cd m$^{-2}$.

Definitions

For convenience, before further description of the present invention, certain terms employed in the specification, examples, and appended claims are collected here.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

The term "aralkyl", as used herein, refers to an alkyl group substituted with an aryl group (e.g., an aromatic or heteroaromatic group).

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths but with at least two carbon atoms. Preferred alkyl groups are lower alkyls. In preferred embodiments, a substituent designated herein as alkyl is a lower alkyl.

The term "aryl" as used herein includes 5-, 6- and 7-membered aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. Also, "DCM" stands for dichloromethane; "rt" stands for room temperature, and may mean about 20° C., about 21° C., about 22° C., about 23° C., about 24° C., about 25° C., or about 26° C.; and "THF" stands for tetrahydrofuran. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "non-coordinating anion" relates to a negatively charged moiety that interacts weakly with cations. Non-coordinating anions are useful in studying the reactivity of electrophilic cations, and are commonly found as counterions for cationic metal complexes with an unsaturated coordination sphere. In many cases, non-coordinating anions have a negative charge that is distributed symmetrically over a number of electronegative atoms. Salts of these anions are often soluble non-polar organic solvents, such as dichloromethane, toluene, or alkanes.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

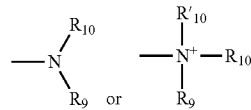

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms, such as nitrogen, may have hydrogen substituents and/or any permissible substituents of organic compounds described herein which satisfy the valencies of the heteroatoms.

For purposes of this invention, the chemical elements are identified in accordance with the Periodic Table of the Elements, CAS version, Handbook of Chemistry and Physics, 67th Ed., 1986-87, inside cover.

EXEMPLIFICATION

The invention may be understood with reference to the following examples, which are presented for illustrative purposes only and which are non-limiting. The substrates utilized in these examples were either commercially available, or were prepared from commercially available reagents.

Example 1—Compounds where Donor/Acceptor Interact Via π-π Conjugation

Table 1 and Table 2 depict compounds that involve a donor (paracyclophane-fused carbazole)-acceptor (R group) interaction through π-π conjugation.

TABLE 1

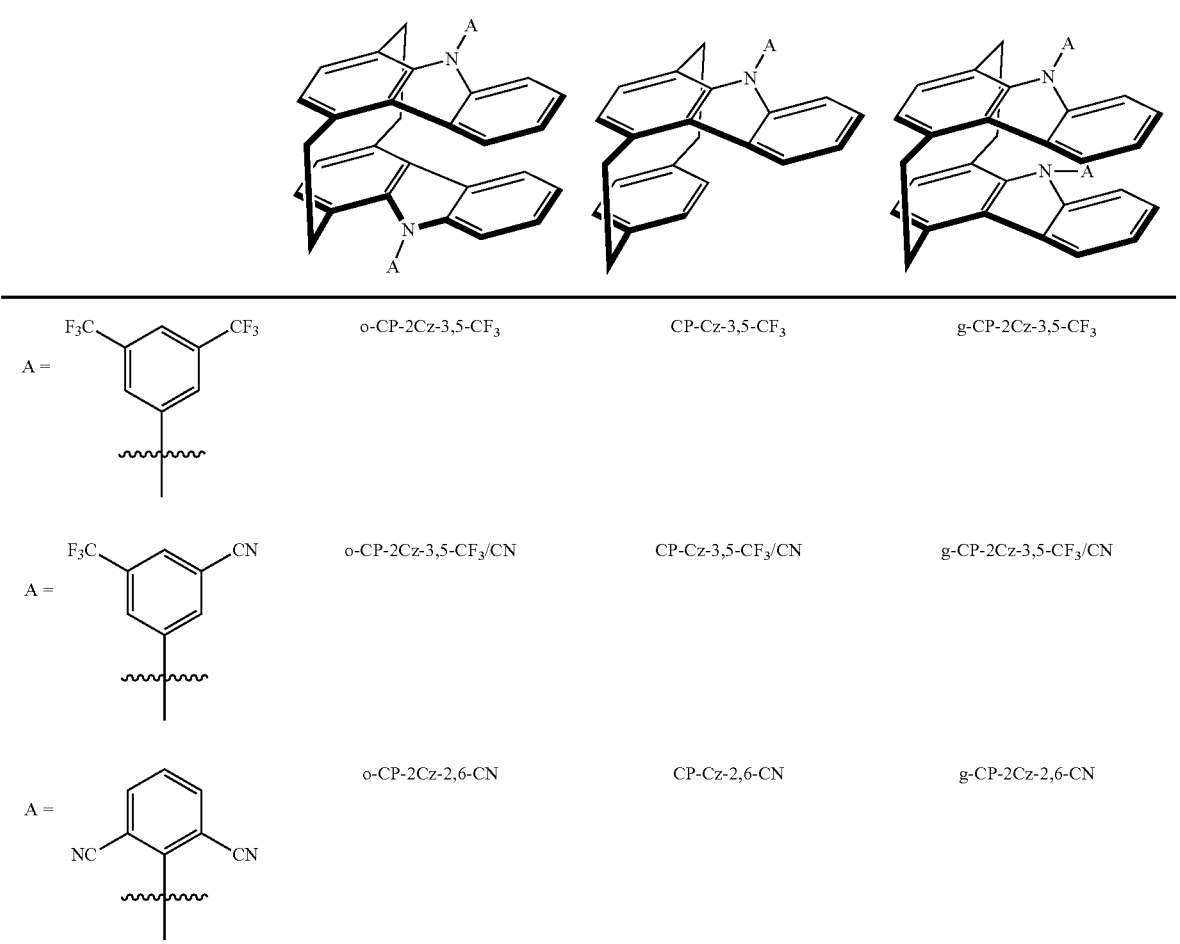

TABLE 1-continued
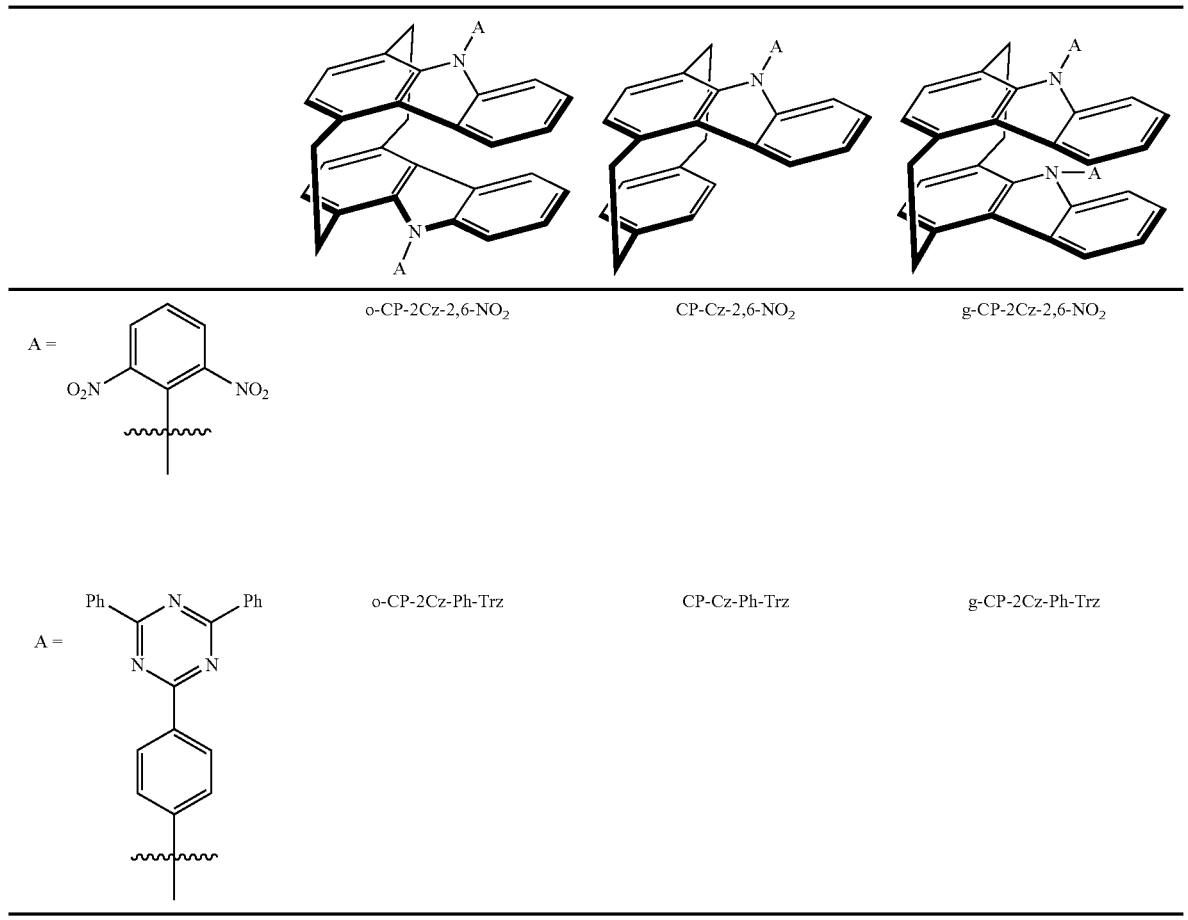
o-CP-2Cz-2,6-NO₂     CP-Cz-2,6-NO₂     g-CP-2Cz-2,6-NO₂
o-CP-2Cz-Ph-Trz     CP-Cz-Ph-Trz     g-CP-2Cz-Ph-Trz
TABLE 2
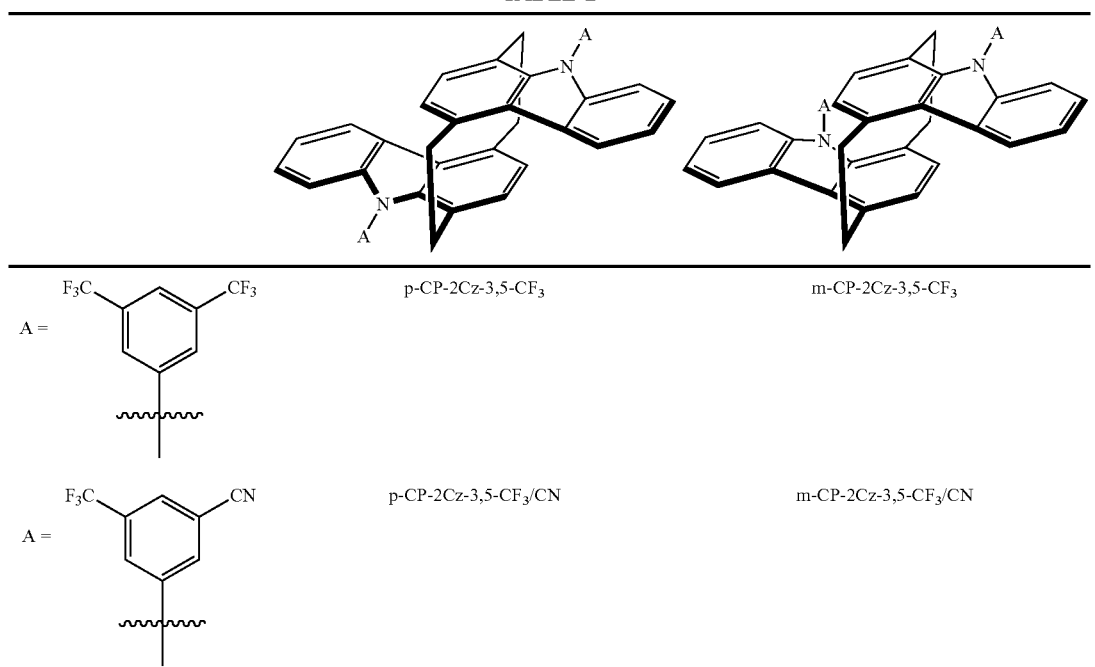
p-CP-2Cz-3,5-CF₃     m-CP-2Cz-3,5-CF₃
p-CP-2Cz-3,5-CF₃/CN     m-CP-2Cz-3,5-CF₃/CN TABLE 2-continued

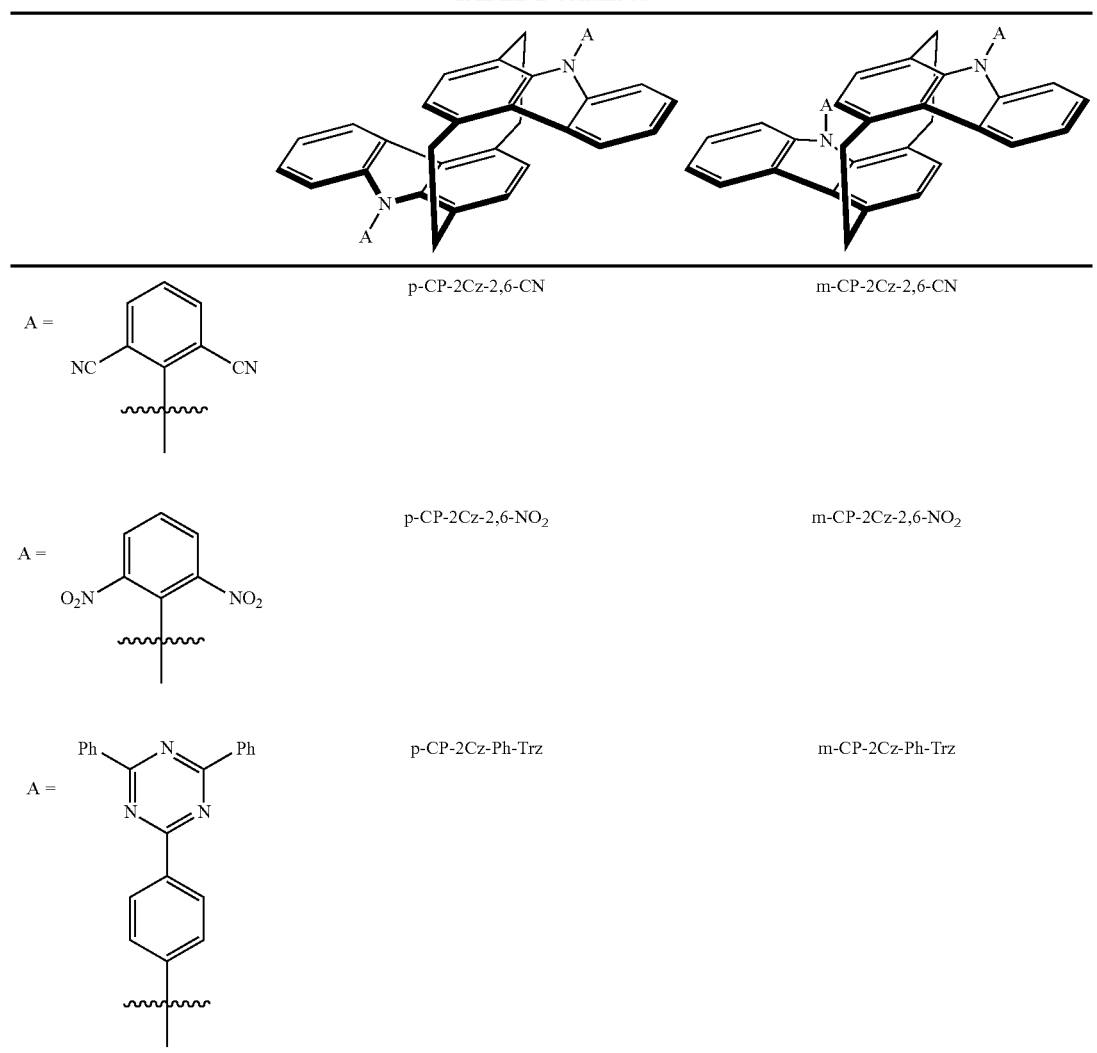

| | | p-CP-2Cz-2,6-CN | m-CP-2Cz-2,6-CN |
|---|---|---|---|
| A = | (NC-C₆H₃-CN) | | |
| A = | (O₂N-C₆H₃-NO₂) | p-CP-2Cz-2,6-NO₂ | m-CP-2Cz-2,6-NO₂ |
| A = | (Ph-Trz-Ph-C₆H₄-) | p-CP-2Cz-Ph-Trz | m-CP-2Cz-Ph-Trz |

Compounds in Table 1 and Table 2 were synthesized, for example, by the following methods.

From o-CP-2Cz, CP-Cz, g-CP-2Cz, p-CP-2Cz, and m-CP-2Cz carbazoles, palladium catalyzed N-arylation of carbazole was applied to store the acceptor group(s). In some cases, $S_NAr$ reaction was employed to establish the C—N bond linkage between carbazole and acceptor group(s).

Figure 5:
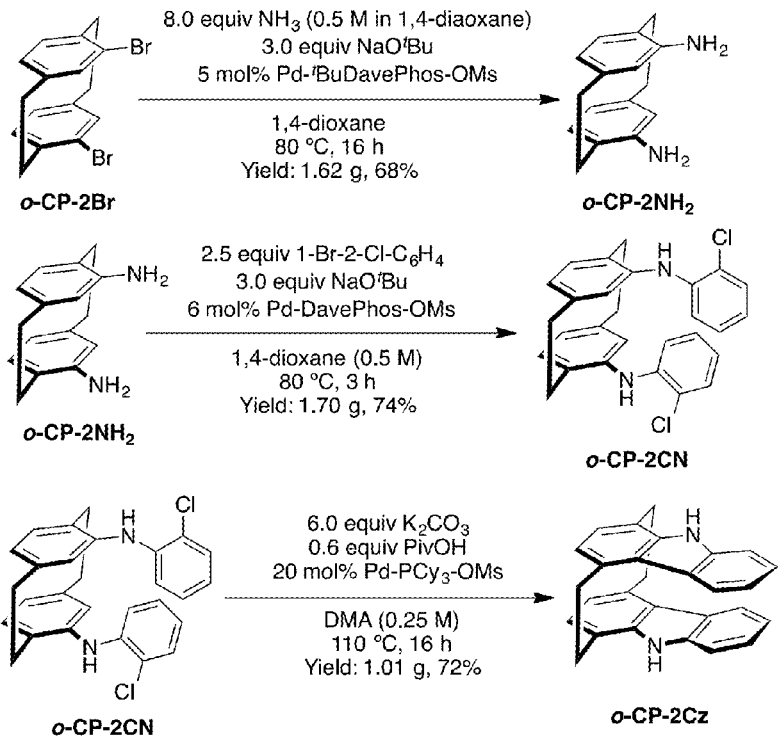
FIG. 5 depicts a reaction scheme showing a synthesis of o-CP-2Cz from commercially available o-CP-2Br (Scheme 1).

Synthesis of o-CP-2Cz from Commercially Available o-CP-2Br (See FIG. 5)

(1) o-CP-2Br to o-CP-2NH$_2$: In a 500-mL Schlenk flask, were placed o-CP-2Br (3.67 g), NaO$^t$Bu (2.90 g), and Pd-$^t$BuDavePhos-OMs (0.36 g). The flask was evacuated/refilled with argon three times and then NH$_3$ solution in 1,4-dioxane (0.5 M, 161 mL) was transferred under argon. The mixture was stirred at 80° C. for 16 h. For work-up, the mixture was diluted with ethyl acetate and then filtered through silica gel. After removing the volatiles of the filtrate, flash chromatography (gradient 0-15% ethyl acetate in hexanes) was used to purify the product. Yield: 1.62 g, 68%.

(2) o-CP-2NH$_2$ to o-CP-2CN: In a 20-mL glass tube equipped with a screw cap, were placed o-CP-2NH$_2$ (1.20 g), NaO$^t$Bu (1.51 g), and Pd-DavePhos-OMs (0.23 g). The tube was evacuated/refilled with argon three times and then added 1-Br-2-Cl—C$_6$H$_4$ (1.50 mL) and 1,4-dioxane (10.0 mL) under argon. The mixture was stirred at 80° C. for 3 h. For work-up, the mixture was diluted with DCM and filtered through silica gel. The volatiles were removed under vacuum, and flash chromatography (gradient 0-5% ethyl acetate in hexanes) was performed to purify the product. Yield: 1.70 g, 74%.

(3) o-CP-2CN to o-CP-2Cz: In a 20-mL glass tube equipped with a screw cap, was placed K$_2$CO$_3$ (1.39 g). The tube was then evacuated under vacuum and flame dried for ca. 1 min. After cooling down to room temperature under vacuum, o-CP-2CN (0.76 g), Pd-PCy$_3$-OMs (0.23 g), and PivOH (0.11 g) were added to the tube. The tube was then capped and evacuate/refill with argon three times. 6.75 mL of anhydrous DMA (N,N-dimethylacetamide) was filled in under argon. The mixture was stirred at 110° C. for 16 h. For work-up, the mixture was diluted with DCM (dichloromethylene) and filtered through silica gel. The filtration was washed with saturatued lithium chloride solution twice and then with saturated sodium chloride solution twice. Flash chromatography (gradient 0 to 30% DCM in hexanes) was used to purify the product. The pure o-CP-2Cz was obtained after DCM/hexanes trituration. Yield: 1.01 g, 72%.

Figure 6:
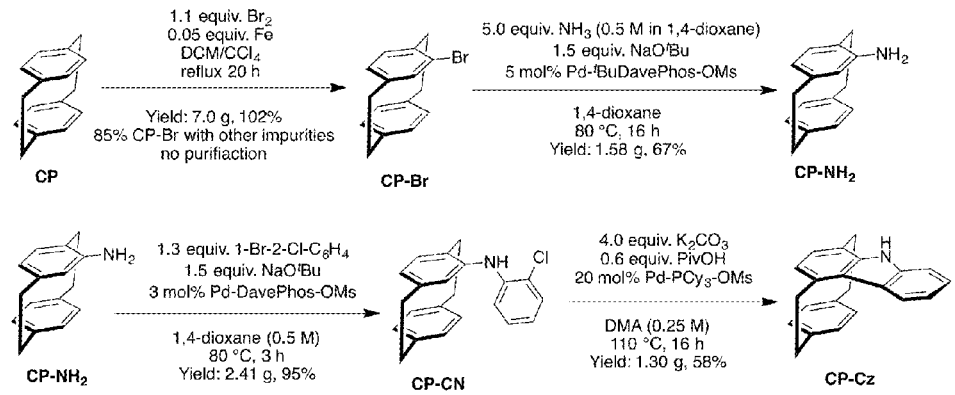
FIG. 6 depicts a reaction scheme showing a synthesis of CP-Cz from [2.2]paracyclophane (Scheme 2).

Synthesis of CP-Cz from [2.2]paracylophane (see FIG. 6)

(1) CP to CP—Br: Modified procedure from literature: Cram et al. *J. Org. Chem.* 1966, 1227. In a 1-L round-bottom flask, was placed iron powder (0.075 g). The flask was then filled with 50 mL of DCM. $Br_2$ (4.5 g) was diluted with 100 mL of $CCl_4$ to make a store solution. 7.5 mL $Br_2$ store solution was added to the 1 L flask and the mixture was allowed to stir at room temperature for 30 min. Then CP ([2.2]paracylophane, 5.0 g) was added as powder followed by transfer of 450 mL of DCM. The mixture was heated to reflux and the rest $Br_2$ solution was added dropwisely to the reflux solution over a period of 1 h. After addition, the mixture was allowed to stir under reflux for 12 h. For work-up, the solution was washed with $NaHSO_3$ (40 mL) two times, and saturated NaCl (150 mL) two times. The organic layer was dried over $MgSO_4$ and volatiles were removed to result in a yellow solid as crude product. Yield: 7.0 g, 102%. The purity of crude product was checked by gas chromatography-mass spectroscopy (GC-MS): ca 85% desired product CP—Br and ca. 15% dibrominated by-products CP-2Br. No further purification was required and the mixture was directly carried to the next-step to synthesize CP—$NH_2$.

(2) CP—Br to CP—$NH_2$: In a 500-mL Schlenk flask, were added CP—Br (2.89 g), NaO$^t$Bu (1.45 g), and Pd-$^t$BuDavePhos-OMs (0.36 g). The flask was evacuated/refilled with argon three times and then $NH_3$ solution in 1,4-dioxane (0.5 M, 102 mL) was transferred under argon. The mixture was stirred at 80° C. for 16 h. For work-up, the mixture was diluted with ethyl acetate and then filtered through silica gel. After removing the volatiles of the filtrate, flash chromatography (gradient 0-10% ethyl acetate in hexanes) was used to purify the product. Yield: 1.58 g, 67%.

(3) CP—$NH_2$ to CP—CN: In a 20-mL glass tube equipped with a screw cap, were placed CP—$NH_2$ (1.56 g), NaO$^t$Bu (1.03 g), and Pd-DavePhos-OMs (0.17 g). The tube was evacuated/refilled with argon three times and then added 1-Br-2-Cl—$C_6H_4$ (1.06 mL) and 1,4-dioxane (14.0 mL) under argon. The mixture was stirred at 80° C. for 3 h. For work-up, the mixture was diluted with DCM and filtered through silica gel. The volatiles were removed under vacuum, and flash chromatography (gradient 0-5% ethyl acetate in hexanes) was used to purify the product. Yield: 2.41 g, 95%.

(4) CP—CN to CP—Cz: In a 300-mL Schlenk flask, was placed $K_2CO_3$ (4.18 g). The flask was then evacuated under vacuum and flame dried for ca. 1 min. After cooling down to room temperature under vacuum, CP—CN (2.53 g), Pd-PCy$_3$-OMs (0.98 g), and PivOH (0.47 g) were added to the tube. The flask was evacuate/refill with argon three times. 30 mL of anhydrous DMA was filled in under argon. The mixture was stirred at 110° C. for 16 h. For work-up, the mixture was diluted with DCM and filtered through silica gel. The filtration was washed with saturated lithium chloride solution twice and then with saturated sodium chloride solution twice. Flash chromatography (gradient 0 to 20% DCM in hexanes) was used to purify the product. The pure CP-Cz was obtained after DCM/hexanes trituration. Yield: 1.30 g, 58%.

Figure 7:
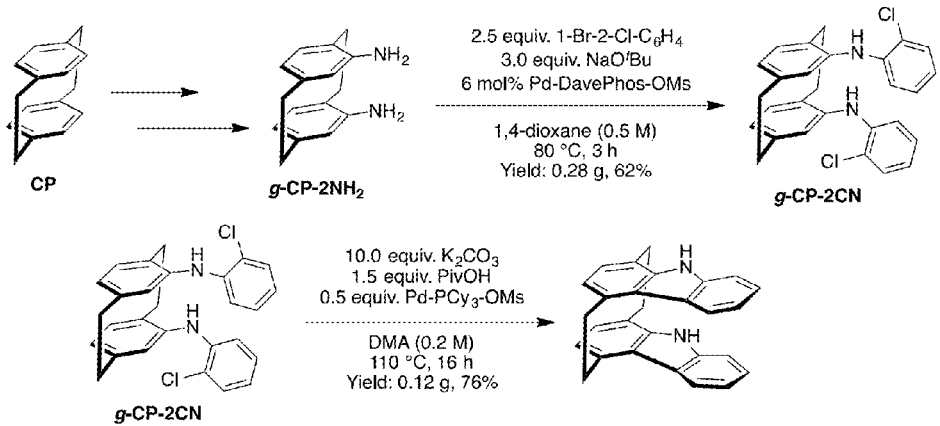
FIG. 7 depicts a reaction scheme showing a synthesis of g-CP-2Cz from CP (Scheme 3).

Synthesis of g-CP-2Cz from CP (see FIG. 7)

Preparation of g-CP-2$NH_2$ from CP following literature: Hopf et al. *Eur. J. Org. Chem.* 2002, 2298.

(1) g-CP-2$NH_2$ to g-CP-2CN: In a 20-mL glass tube equipped with a screw cap, were placed g-CP-2$NH_2$ (0.25 g), NaO$^t$Bu (0.30 g), and Pd-DavePhos-OMs (0.051 g). The tube was evacuated/refilled with argon three times and then added 1-Br-2-Cl—$C_6H_4$ (0.31 mL) and 1,4-dioxane (4.0 mL) under argon. The mixture was stirred at 80° C. for 3 h. For work-up, the mixture was diluted with DCM and filtered through silica gel. The volatiles were removed under vacuum, and flash chromatography (gradient 0-5% ethyl acetate in hexanes) was used to purify the product. Yield: 0.29 g, 62%.

(2) g-CP-2CN to g-CP-2Cz: In a 20-mL glass tube equipped with a screw cap, was placed $K_2CO_3$ (0.66 g). The tube was then evacuated under vacuum and flame dried for ca. 1 min. After cooling down to room temperature under vacuum, g-CP-2CN (0.19 g), Pd-PCy$_3$-OMs (0.15 g), and PivOH (0.072 g) were added to the tube. The tube was then capped and evacuate/refill with argon three times. 2.5 mL of anhydrous DMA was filled in under argon. The mixture was stirred at 110° C. for 16 h. For work-up, the mixture was diluted with DCM and filtered through silica gel. The filtration was washed with saturatued lithium chloride solution twice and then with saturated sodium chloride solution twice. Flash chromatography (gradient 0 to 40% DCM in hexanes) was used to purify the product. The pure g-CP-2Cz was obtained after DCM/hexanes trituration. Yield: 0.12 g, 76%.

Figure 8:
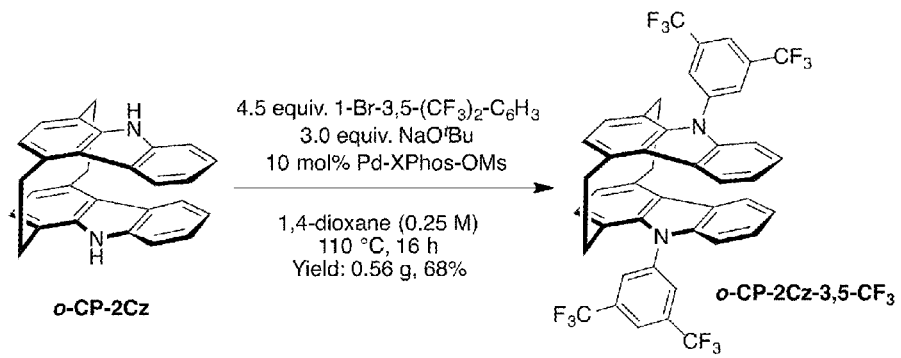
FIG. 8 depicts a reaction scheme showing a synthesis of o-CP-2Cz-3,5-CF$_3$ (Scheme 4).

Synthesis of [2.2]paracylcophane Derived Donor-Acceptor Compounds (Selected Examples in Table 1 and Table 2)

o-CP-2Cz-3,5-$CF_3$ (see FIG. 8)

In a 20-mL glass tube equipped with a screw cap, were placed o-CP-2Cz (0.39 g), NaO$^t$Bu (0.32 g), and Pd-XPhos-OMs (0.090 g). The tube was then capped and evacuate/refill with argon three times. 0.79 mL of 1-Br-3,5-$(CF_3)_2$—$C_6H_3$ and 4.0 mL of anhydrous 1,4-dioxane were filled in under argon. The mixture was stirred at 110° C. for 16 h. For work-up, the mixture was diluted with DCM and filtered through silica gel. After removing the volatiles, flash chromatography (gradient 0 to 10% DCM in hexanes) was used to purify the product. Yield: 0.56 g, 68%.

Figure 9:
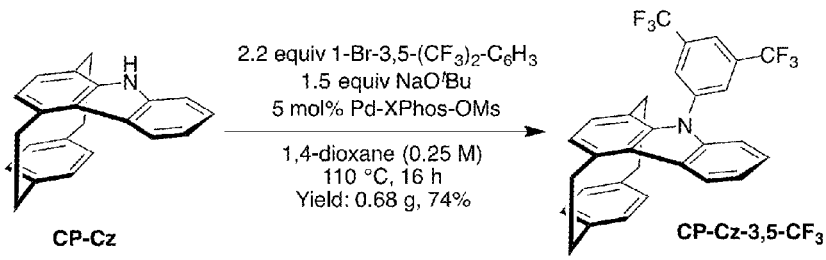
FIG. 9 depicts a reaction scheme showing a synthesis of CP-Cz-3,5-CF$_3$ (Scheme 5).

CP-Cz-3,5-$CF_3$ (see FIG. 9)

Figure 10:
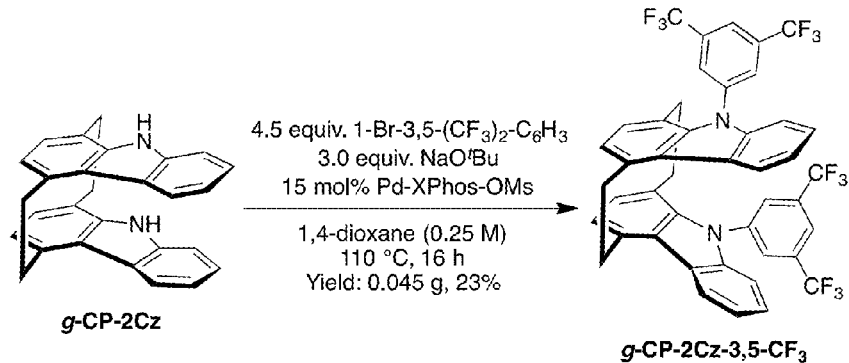
FIG. 10 depicts a reaction scheme showing a synthesis of g-CP-Cz-3,5-CF$_3$ (Scheme 6).

In a 20-mL glass tube equipped with a screw cap, were placed CP-Cz (0.54 g), NaO$^t$Bu (0.28 g), and Pd-XPhos-OMs (0.080 g). The tube was then capped and evacuate/refill with argon three times. 0.73 mL of 1-Br-3,5-$(CF_3)_2$—$C_6H_3$ and 7.0 mL of anhydrous 1,4-dioxane were filled in under argon. The mixture was stirred at 110° C. for 16 h. For work-up, the mixture was diluted with DCM and filtered through silica gel. After removing the volatiles, flash chromatography (gradient 0 to 10% DCM in hexanes) was used to purify the product. Yield: 0.68 g, 74%.

g-CP-Cz-3,5-CF$_3$ (see FIG. 10)

Figure 11:
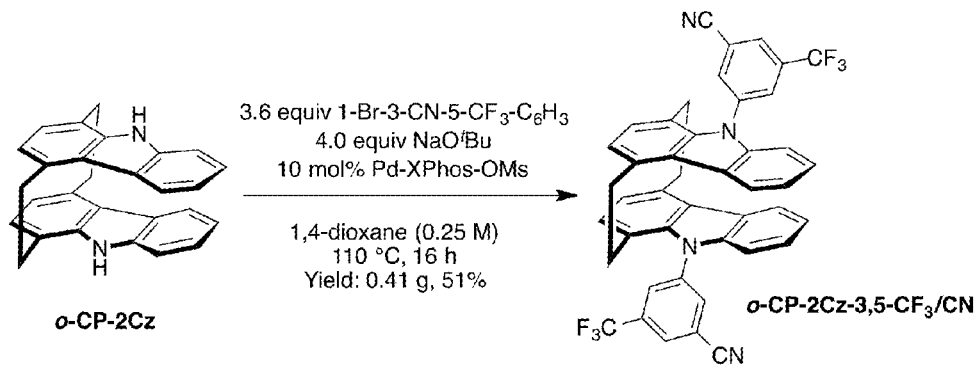
FIG. 11 depicts a reaction scheme showing a synthesis of o-CP-2Cz-3,5-CF$_3$/CN (Scheme 7).

In a 20-mL glass tube equipped with a screw cap, were placed g-CP-2Cz (0.092 g), NaO$^t$Bu (0.090 g), and Pd-XPhos-OMs (0.028 g). The tube was then capped and evacuate/refill with argon three times. 0.22 mL of 1-Br-3,5-(CF$_3$)$_2$—C$_6$H$_3$ and 1.5 mL of anhydrous 1,4-dioxane were filled in under argon. The mixture was stirred at 110° C. for 16 h. For work-up, the mixture was diluted with DCM and filtered through silica gel. After removing the volatiles, flash chromatography (gradient 0 to 15% DCM in hexanes) was used to purify the product. Yield: 0.045 g, 23%.

o-CP-2Cz-3,5-CF$_3$/CN (see FIG. 11)

In a 20-mL glass tube equipped with a screw cap, were placed o-CP-2Cz (0.39 g), NaO$^t$Bu (0.39 g), and Pd-XPhos-OMs (0.097 g). The tube was then capped and evacuate/refill with argon three times. 0.53 mL of 1-Br-3-CN-5-CF$_3$—C$_6$H$_3$ and 4.0 mL of anhydrous 1,4-dioxane were filled in under argon. The mixture was stirred at 110° C. for 16 h. For work-up, the mixture was diluted with DCM and filtered through silica gel. After removing the volatiles, flash chromatography (gradient 0 to 20% DCM in hexanes) was used to purify the product. Yield: 0.41 g, 51%.

Figure 12:
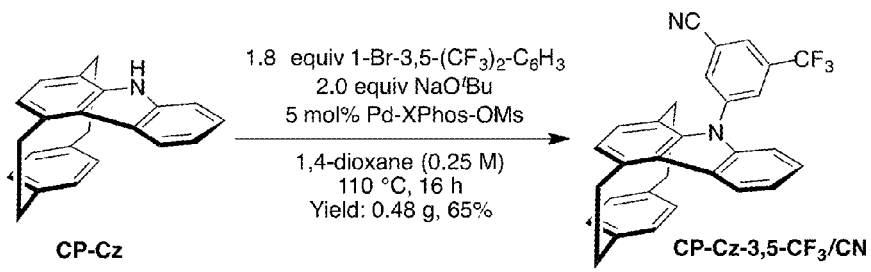
FIG. 12 depicts a reaction scheme showing a synthesis of CP-Cz-3,5-CF$_3$/CN (Scheme 8).

CP-Cz-3,5-CF$_3$/CN (see FIG. 12)

In a 20-mL glass tube equipped with a screw cap, were placed CP-Cz (0.45 g), NaO$^t$Bu (0.29 g), and Pd-XPhos-OMs (0.069 g). The tube was then capped and evacuate/refill with argon three times. 0.39 mL of 1-Br-3-CN-5-CF$_3$—C$_6$H$_3$ and 5.0 mL of anhydrous 1,4-dioxane were filled in under argon. The mixture was stirred at 110° C. for 16 h. For work-up, the mixture was diluted with DCM and filtered through silica gel. After removing the volatiles, flash chromatography (gradient 0 to 20% DCM in hexanes) was used to purify the product. Yield: 0.48 g, 65%.

Figure 13:
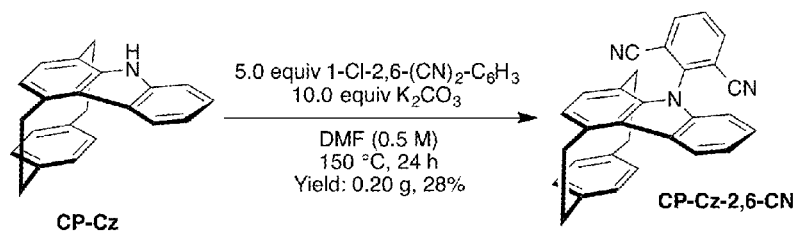
FIG. 13 depicts a reaction scheme showing a synthesis of CP-Cz-2,6-CN (Scheme 9).

CP-Cz-2,6-CN (see FIG. 13)

In a 20-mL glass tube equipped with a screw cap, were placed CP-Cz (0.45 g), K$_2$CO$_3$ (2.13 g), and 1-Cl-2,6-(CN)$_2$—C$_6$H$_3$ (1.23 g). The tube was then capped and evacuate/refill with argon three times. 3.0 mL of anhydrous DMF (N,N-dimethylformamide) was filled in under argon. The mixture was stirred at 150° C. for 24 h. For work-up, the mixture was diluted with DCM and filtered through silica gel. The filtrate was washed with saturated NaCl solution twice and organic layer was dried over MgSO$_4$. After removing the volatiles, flash chromatography (gradient 0 to 40% ethyl acetate in hexanes) was used to purify the product. Yield: 0.20 g, 28%.

Figure 14:
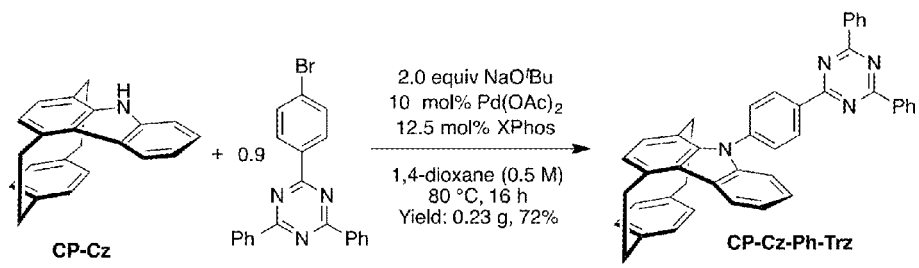
FIG. 14 depicts a reaction scheme showing a synthesis of CP-Cz-Ph-Trz (Scheme 10).

CP-Cz-Ph-Trz (see FIG. 14)

In a 20-mL glass tube equipped with a screw cap, were placed CP-Cz (0.11 g), 2-parabromophenyl-4,6-diphenyl-1,3,5-triazine (Trz-Ph-Br, 0.12 g), NaO$^t$Bu (0.065 g), Pd(OAc)$_2$ (0.014 g), and XPhos (0.037 g). The tube was then capped and evacuate/refill with argon three times. 0.6 mL of anhydrous 1,4-dioxane was filled in under argon. The mixture was stirred at 80° C. for 16 h. For work-up, the mixture was diluted with DCM and filtered through silica gel. After removing the volatiles, flash chromatography (gradient 0 to 30% DCM in hexanes) was used to purify the product. Yield: 0.23 g, 72%.

Example 2—Compounds where Donor/Acceptor Interact Via Spatial Proximity

Table 3, Table 4, and Table 5 depict compounds that involve a donor (R-substituted top ring)-acceptor (heteroaromatic group or triazine-substituted phenylene) interaction through spatial proximity.

TABLE 3

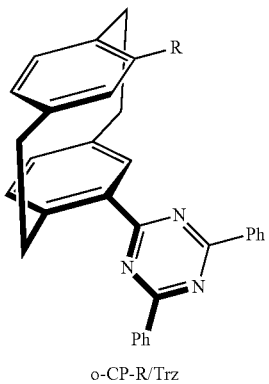

o-CP-R/Trz

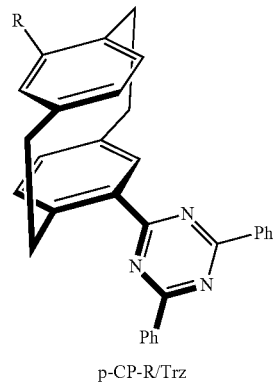

p-CP-R/Trz

R = H, NH$_2$, NMe$_2$, OMe, NPh$_2$, and N-carbazolyl, N-iminodibenzyl, N-iminostilbene, N-(10H-phenothiazine), N-(10H-phenoxazine), N-(9H-3,9'-bicarbazole), N-(7,12-dihydro-5H-7,12-[1,2]benzenonaphtho[2,3-b]carbazole), and other electron-donating aromatics or heteroaromatics.

TABLE 3-continued

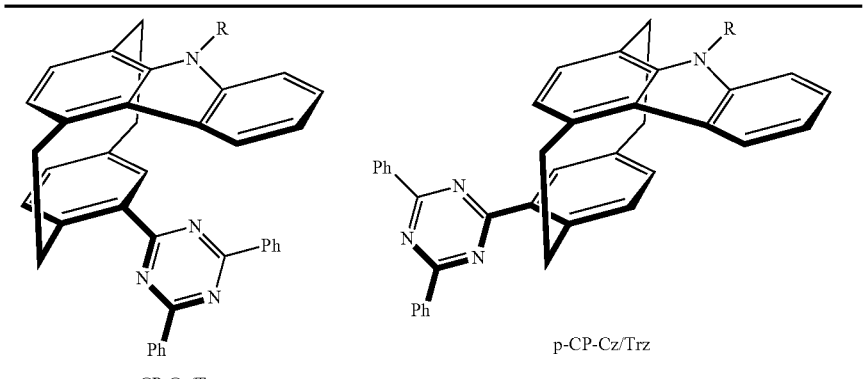

o-CP-Cz/Trz  p-CP-Cz/Trz

R = H, Me, Aryl (Ph, 3,5-(CF$_3$)$_2$—C$_6$H$_3$, 3,5-(CH$_3$)$_2$—C$_6$H$_3$, etc.)

TABLE 4

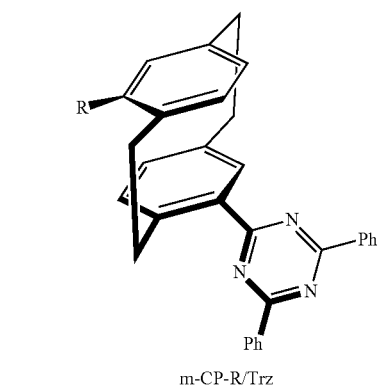

m-CP-R/Trz

R = H, NH$_2$, NMe$_2$, OMe, NPh$_2$, and N-carbazolyl, N-iminodibenzyl, N-iminostilbene, N-(10H-phenothiazine), N-(10H-phenoxazine), N-(9H-3,9'-bicarbazole), N-(7,12-dihydro-5H-7,12-[1,2]benzenonaphtho[2,3-b]carbazole), and other electron-donating aromatics or heteroaromatics.

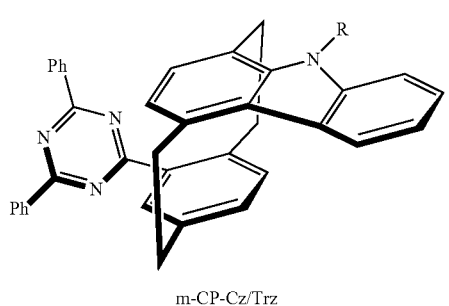

m-CP-Cz/Trz

R = H, Me, Aryl (Ph, 3,5-(CF$_3$)$_2$—C$_6$H$_3$, 3,5-(CH$_3$)$_2$—C$_6$H$_3$, etc.)

TABLE 5

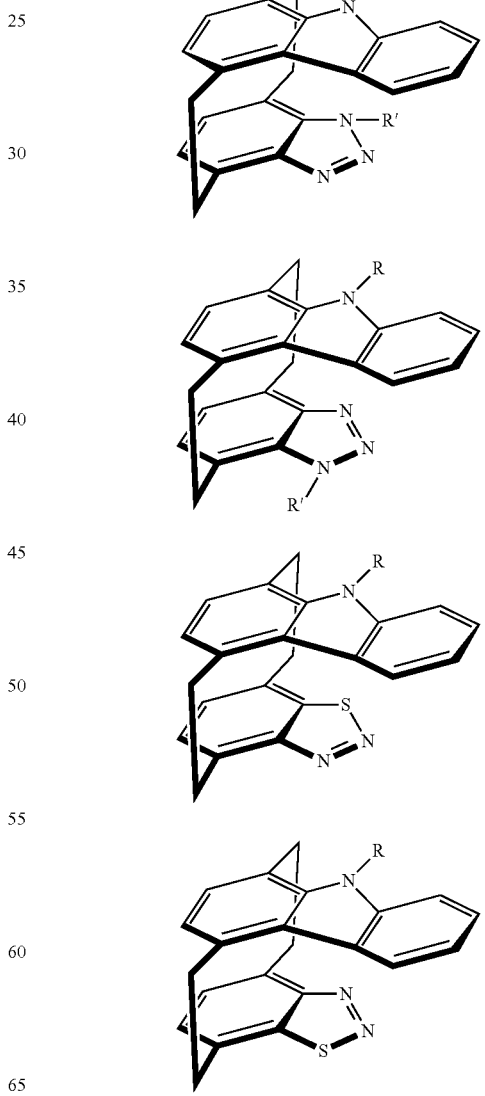

TABLE 5-continued
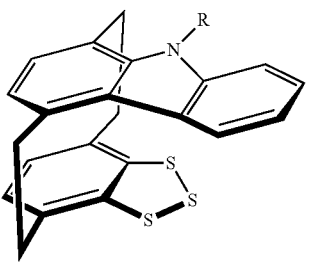
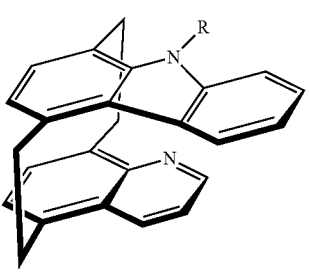
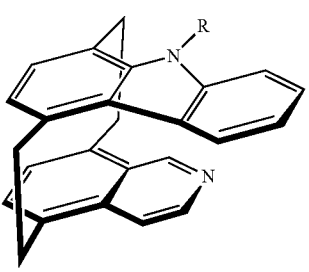
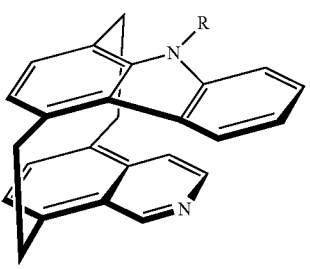
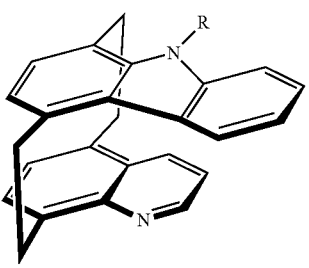
TABLE 5-continued
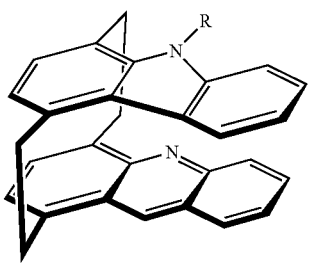
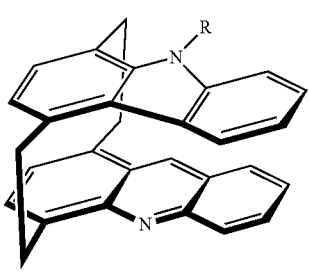
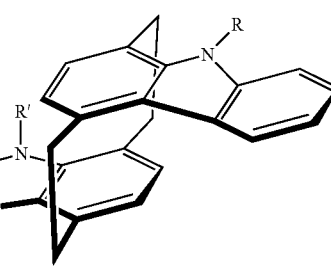
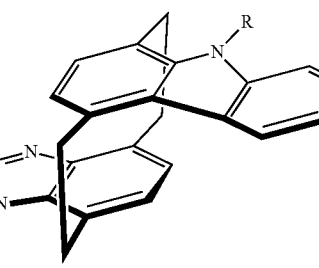
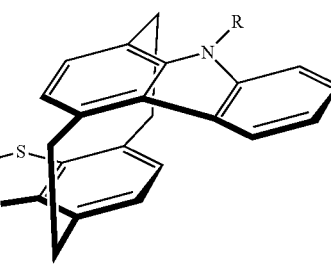

TABLE 5-continued

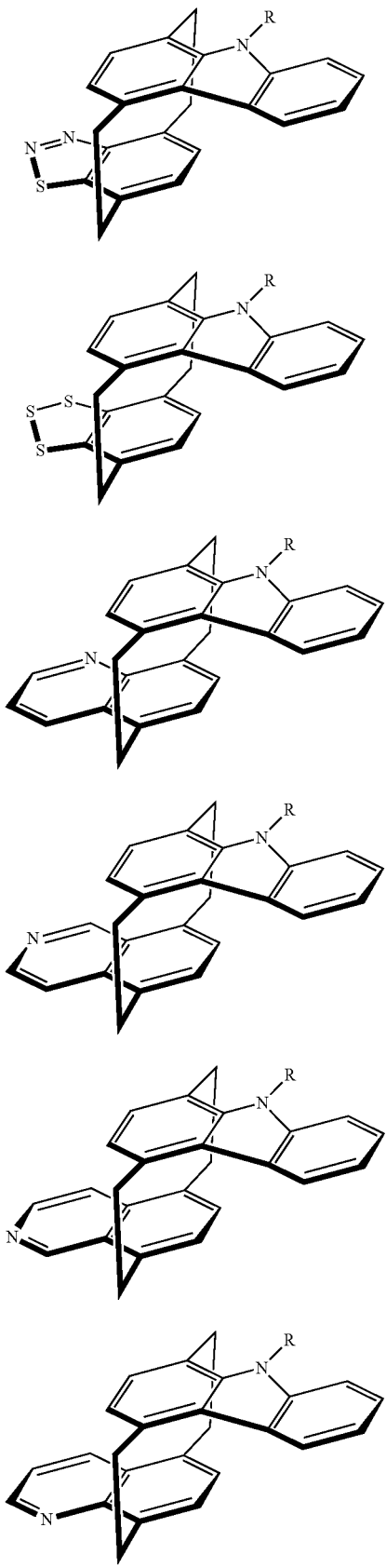

TABLE 5-continued

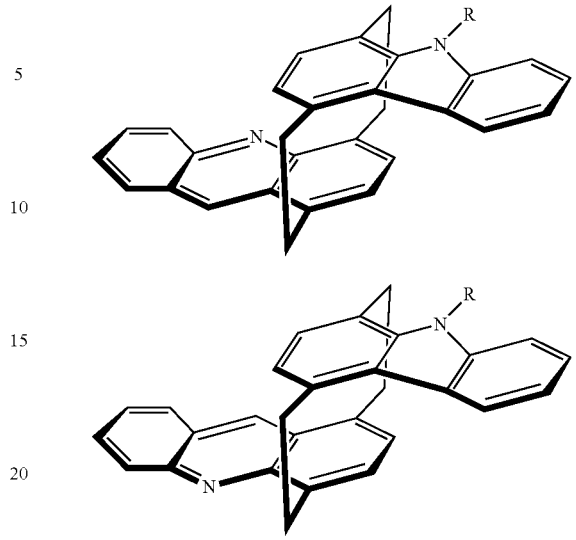

Syntheses of selected compounds from Tables 3, 4, and 5 are described below.

Scheme 11. Synthesis of CP-H/Trz

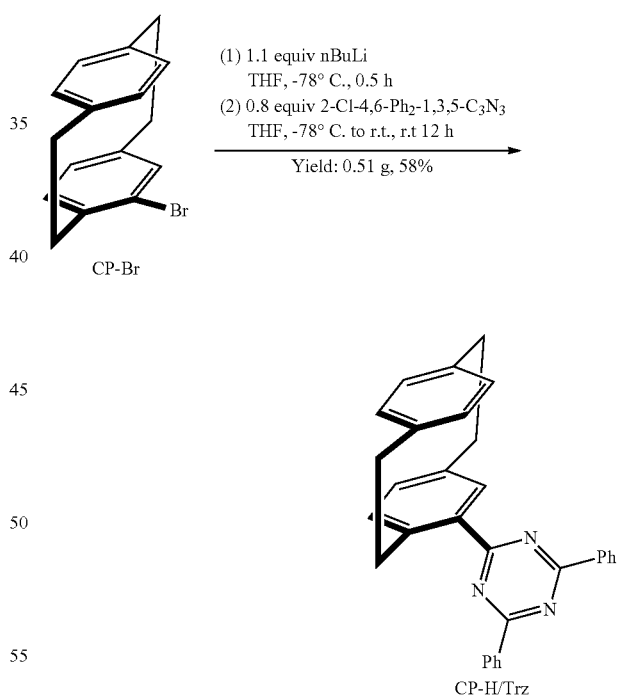

In a 250-mL round-bottom flask, was added CP—Br (0.70 g) and transferred 20 mL of anhydrous THF (tetrahydrofuran). The solution was placed in a dry ice/acetone bath for 15 min before dropwisely adding nBuLi (2.5 M in n-hexane, 1.04 mL) to result in a yellow slurry. The reaction mixture was allowed to stir at −78° C. for 0.5 h. Then THF solution (20 mL) of 2-Cl-4,6-Ph$_2$-1,3,5-C$_3$N$_3$ (0.53 g) was slowly transferred into the yellow slurry over a period of 5 min. After addition, the mixture was allowed to warm up to room temperature and stirred for 12 h. For work-up, the reaction mixture was quenched by saturated NH₄Cl solution and organic layer was washed by NH₄Cl solution twice followed by saturated NaCl twice and dried over MgSO₄. After removing volatiles, the crude product was purified by flash chromatography (gradient 0-20% DCM in hexanes). Yield: 0.51 g, 58%.

(2) o-CP—Br/Trz to o-CP—NH₂/Trz: In a 200-mL Schlenk flask, were added o-CP—Br/Trz (1.55 g), NaO^tBu (1.41 g), and Pd-^tBuDavePhos-OMs (0.22 g). The flask was evacuated/refilled with argon three times and then NH₃ solution in 1,4-dioxane (0.5 M, 34.0 mL) was transferred under argon. The mixture was stirred at 80° C. for 16 h. For work-up, the mixture was diluted with ethyl acetate and then filtered through silica gel. After removing the volatiles of the filtrate, flash chromatography (gradient 0-10% ethyl acetate in hexanes) was used to purify the product. Yield: 1.20 g, 86%.

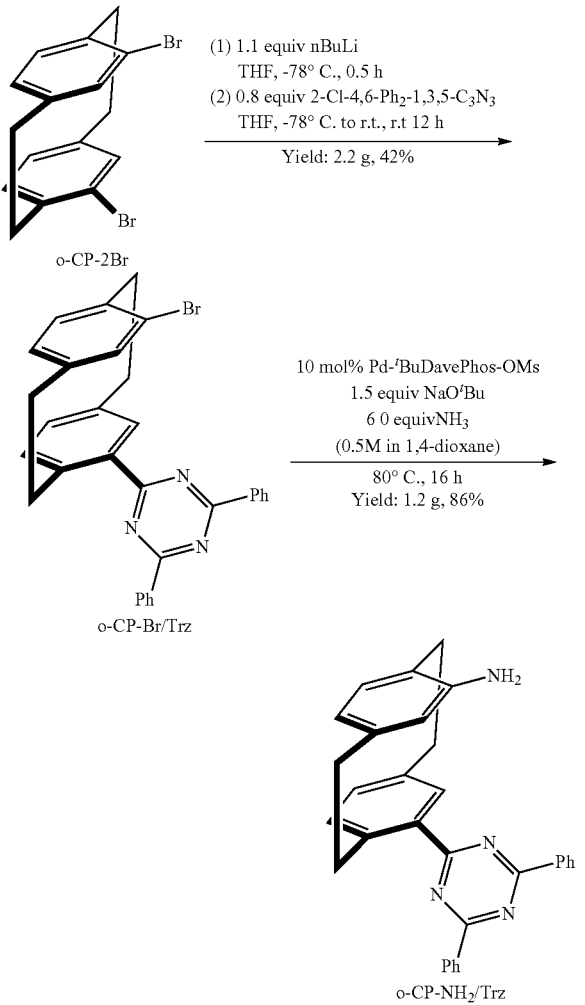

Scheme 12. Synthesis of o-CP-NH₂/Trz

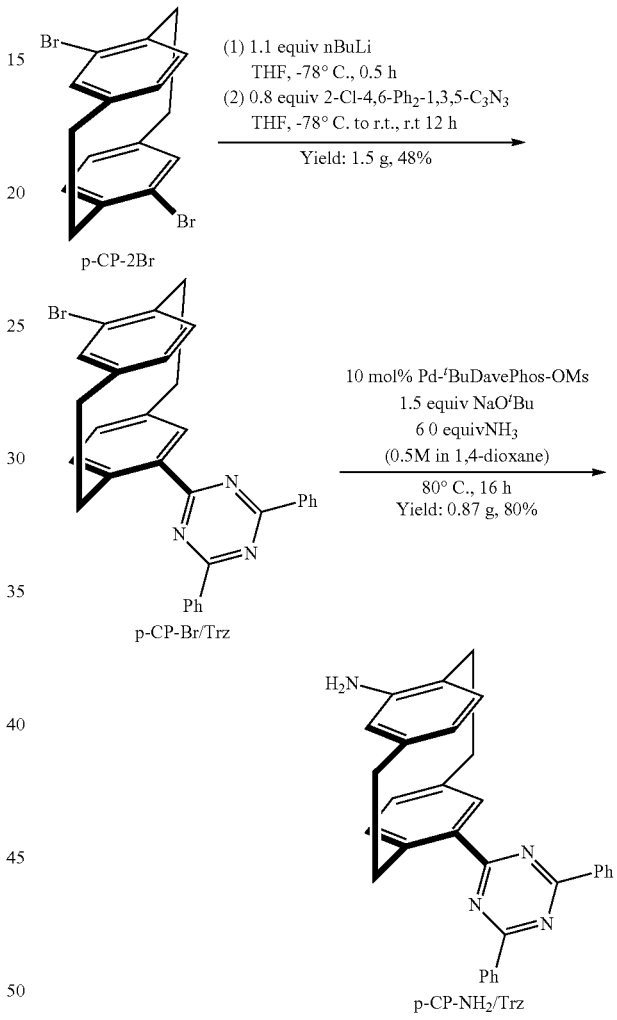

Scheme 13. Synthesis of p-CP-NH₂/Trz (1) o-CP-2Br to o-CP—Br/Trz: In a 500-mL round-bottom flask, was added o-CP-2Br (4.21 g) and transferred 50 mL of anhydrous THF. The solution was placed in a dry ice/acetone bath for 15 min before dropwisely adding nBuLi (2.5 M in n-hexane, 5.0 mL) to result in a yellow slurry. The reaction mixture was allowed to stir at −78° C. for 0.5 h. Then THF solution (50 mL) of 2-Cl-4,6-Ph₂-1,3,5-C₃N₃ (2.68 g) was slowly transferred into the yellow slurry over a period of 5 min. After addition, the mixture was allowed to warm up to room temperature and stirred for 12 h. For work-up, the reaction mixture was quenched by saturated NH₄Cl solution and organic layer was washed by NH₄Cl solution twice followed by saturated NaCl twice and dried over MgSO₄. After removing volatiles, the crude product was purified by flash chromatography (gradient 0-20% DCM in hexanes). Yield: 2.2 g, 42%.

(1) p-CP-2Br to p-CP—Br/Trz: In a 500-mL round-bottom flask, was added p-CP-2Br (2.20 g) and transferred 250 mL of anhydrous THF. The solution was placed in dry ice/acetone bath for 15 min before dropwisely adding nBuLi (2.5 M in n-hexane, 5.2 mL) to result in a yellow slurry. The reaction mixture was allowed to stir at −78° C. for 0.5 h. Then THF solution (30 mL) of 2-Cl-4,6-Ph₂-1,3,5-C₃N₃ (2.68 g) was slowly transferred into the yellow slurry over a period of 5 min. After addition, the mixture was allowed to warm up to room temperature and stirred for 12 h. For work-up, the reaction mixture was quenched by saturated NH₄Cl solution and organic layer was washed by NH₄Cl solution twice followed by saturated NaCl twice and dried over MgSO₄. After removing volatiles, the crude product was purified by flash chromatography (gradient 0-20% DCM in hexanes). Yield: 1.5 g, 48%.

(2) p-CP—Br/Trz to p-CP—NH$_2$/Trz: In a 200-mL Schlenk flask, were added p-CP—Br/Trz (1.04 g), NaO$^t$Bu (0.33 g), and Pd-$^t$BuDavePhos-OMs (0.14 g). The flask was evacuated/refilled with argon three times and then NH$_3$ solution in 1,4-dioxane (0.5 M, 21.0 mL) was transferred under argon. The mixture was stirred at 80° C. for 16 h. For work-up, the mixture was diluted with ethyl acetate and then filtered through silica gel. After removing the volatiles of the filtrate, flash chromatography (gradient 0-20% ethyl acetate in hexanes) was used to purify the product. Yield: 0.87 g, 80%.

Scheme 14. Synthesis of o-CP-Cz/Trz

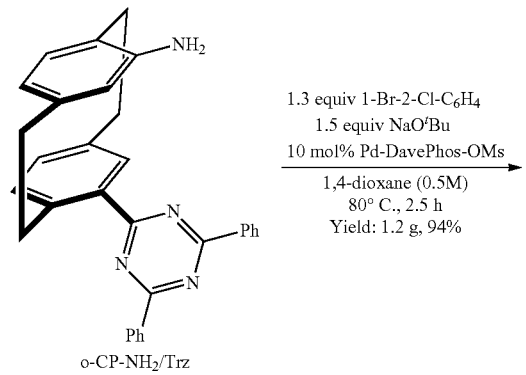

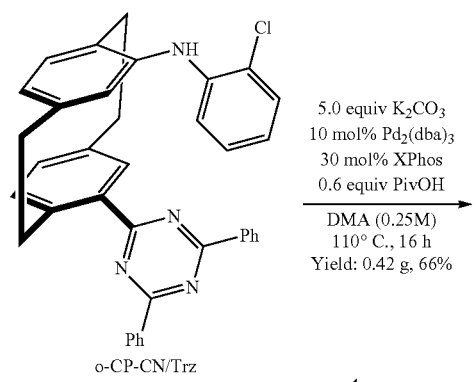

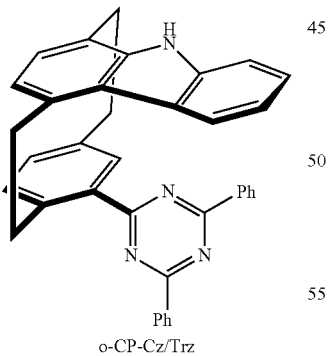

(1) o-CP—NH$_2$/Trz to o-CP—CN/Trz: In a 20-mL glass tube equipped with a screw cap, was placed o-CP—NH$_2$/Trz (1.00 g), NaO$^t$Bu (1.35 g), and Pd-DavePhos-OMs (0.15 g). The tube was evacuated/refilled with argon three times and then added 1-Br-2-Cl—C$_6$H$_4$ (0.34 mL) and 1,4-dioxane (4.5 mL) under argon. The mixture was stirred at 80° C. for 2.5 h. For work-up, the mixture was diluted with DCM and filtered through silica gel. The volatiles were removed under vacuum, and flash chromatography (gradient 0-20% ethyl acetate in hexanes) was used to purify the product. Yield: 1.2 g, 94%.

(2) o-CP—CN/Trz to o-CP-Cz/Trz: In a 20-mL glass tube equipped with a screw cap, was placed K$_2$CO$_3$ (0.69 g). The tube was then evacuated under vacuum and flame dried for ca. 1 min. After cooling down to room temperature under vacuum, o-CP—CN/Trz (0.57 g), Pd$_2$(dba)$_3$ (0.09 g), XPhos (0.14 g), and PivOH (0.06 g) were added to the tube. The tube was then capped and evacuate/refill with argon three times. 4.0 mL of anhydrous DMA was filled in under argon. The mixture was stirred at 110° C. for 16 h. For work-up, the mixture was diluted with DCM and filtered through silica gel. The filtration was washed with saturatued lithium chloride solution twice and then with saturated sodium chloride solution twice. Flash chromatography (gradient 0 to 20% DCM in hexanes) was used to purify the product. Yield: 0.42 g, 66%.

Scheme 15. Synthesis of p-CP-NPh$_2$/Trz

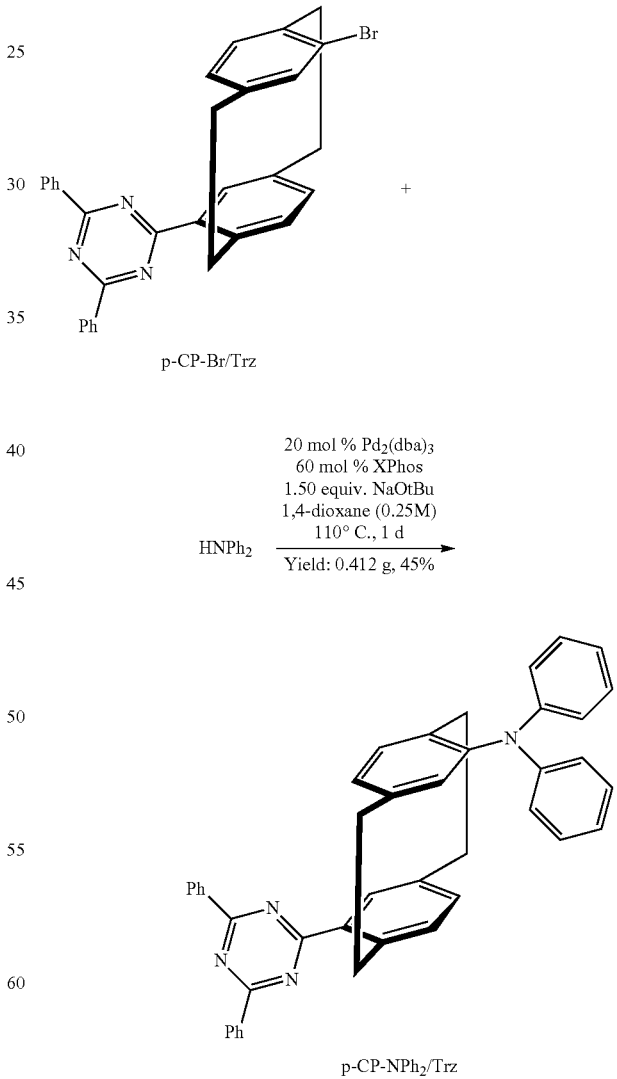

In a 20-mL glass tube equipped with a screw cap, was placed p-CP—Br/Trz (0.88 g), diphenylamine (0.26 g), NaOtBu (0.24 g), Pd$_2$(dba)$_3$ (dba=dibenzylideneacetone, 0.31 g) and XPhos (0.49 g). The tube was evacuated/refilled with argon three times and then added 1,4-dioxane (7.0 mL) under argon. The mixture was stirred at 110° C. for 1 d. For work-up, the mixture was diluted with DCM and filtered through silica gel. The volatiles were removed under vacuum, and flash chromatography (gradient 0-20% dichloromethane in hexanes) was used to purify the product. The curde product obtained from chromatography was further purified by trituration with methanol. Yield: 0.41 g, 45%.

Photoluminescent characterization of p-CP—NPh$_2$/Trz: maximum emission wavelength: 481 nm (in toluene, r.t.); Photoluminescent quantum yields (PLQY): 0.75 (under air, in toluene), 0.89 (under N$_2$, in toluene).

In a 20-mL glass tube equipped with a screw cap, was placed p-CP—Br/Trz (0.104 g), carbazole (0.030 g), NaOtBu (0.025 g), Pd$_2$(dba)$_3$ (0.037 g) and tBuXPhos (0.051 g). The tube was evacuated/refilled with argon three times and then added 1,4-dioxane (1.0 mL) under argon. The mixture was stirred at 110° C. for 1 d. For work-up, the mixture was diluted with DCM and filtered through silica gel. The volatiles were removed under vacuum, and flash chromatography (gradient 0-30% dichloromethane in hexanes) was used to purify the product. The curde product obtained from chromatography was further purified by trituration with methanol. Yield: 0.040 g, 37%.

Scheme 16. Synthesis of p-CP-(N-Cz)/Trz

Scheme 17. Synthesis of p-CP-(N-CzCz)/Trz

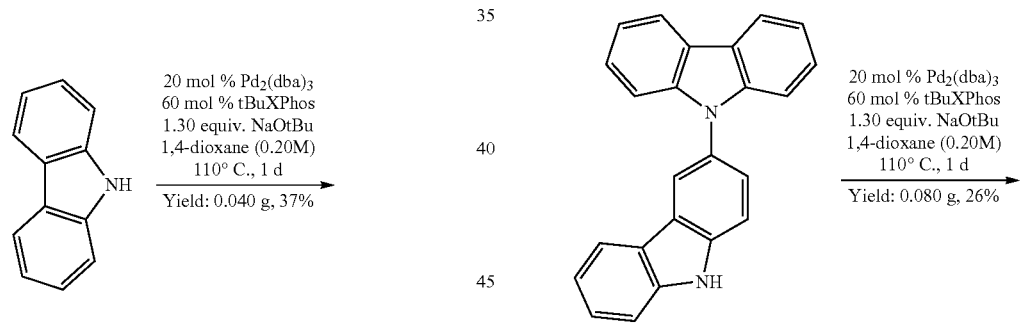

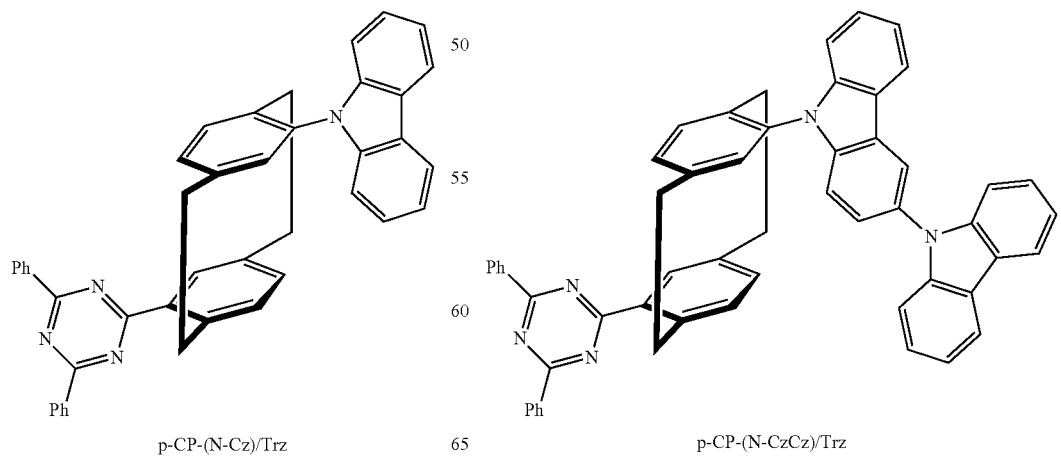

In a 20-mL glass tube equipped with a screw cap, was placed p-CP—Br/Trz (0.259 g), 9H-3,9'-bicarbazole (0.133 g), NaO$^t$Bu (0.063 g), Pd$_2$(dba)$_3$ (0.092 g) and tBuXPhos (0.133 g). The tube was evacuated/refilled with argon three times and then added 1,4-dioxane (2.5 mL) under argon. The mixture was stirred at 110° C. for 1 d. For work-up, the mixture was diluted with DCM and filtered through silica gel. The volatiles were removed under vacuum, and flash chromatography (gradient 0-30% dichloromethane in hexanes) was used to purify the product. The curde product obtained from chromatography was further purified by trituration with methanol. Yield: 0.080 g, 26%.

Photoluminescent characterization of p-CP—(N-CzCz)/Trz: maximum emission wavelength: 438 nm (in toluene, r.t.), 514 nm (in dichloromethane, r.t.), 456 nm (thin film); Photoluminescent quantum yields (PLQY): 0.08 (under air, in toluene), 0.20 (under N$_2$, in toluene).

In a 20-mL glass tube equipped with a screw cap, was placed p-CP—Br/Trz (0.104 g), iminodibenzyl (0.031 g), NaO$^t$Bu (0.025 g), Pd$_2$(dba)$_3$ (0.037 g) and RuPhos (0.056 g). The tube was evacuated/refilled with argon three times and then added 1,4-dioxane (1.0 mL) under argon. The mixture was stirred at 110° C. for 1 d. For work-up, the mixture was diluted with DCM and filtered through silica gel. The volatiles were removed under vacuum, and flash chromatography (gradient 0-30% dichloromethane in hexanes) was used to purify the product. Yield: 0.040 g, 40%.

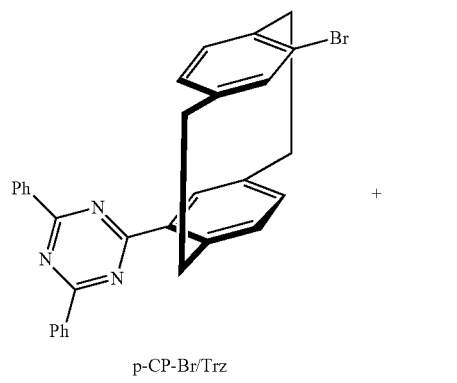

Scheme 18. Synthesis of p-CP-(N-Idb)/Trz

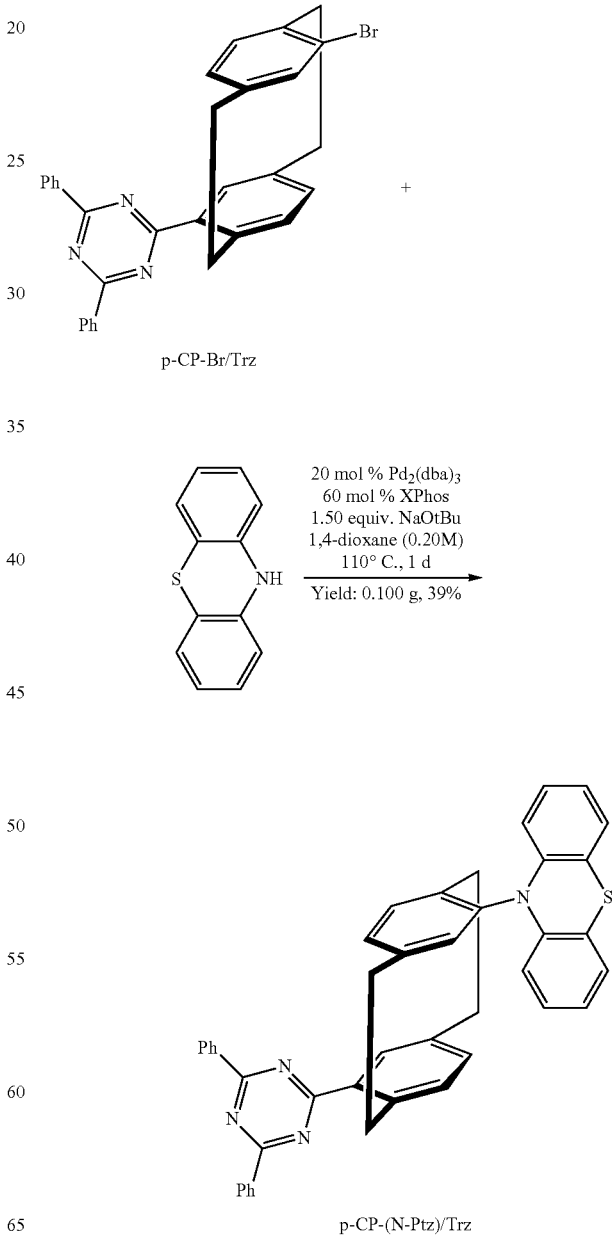

Scheme 19. Synthesis of p-CP-(N-Ptz)/Trz

In a 20-mL glass tube equipped with a screw cap, was placed p-CP—Br/Trz (0.259 g), phenothiazine (0.080 g), NaO$^t$Bu (0.063 g), Pd$_2$(dba)$_3$ (0.092 g) and XPhos (0.143 g). The tube was evacuated/refilled with argon three times and then added 1,4-dioxane (2.5 mL) under argon. The mixture was stirred at 110° C. for 1 d. For work-up, the mixture was diluted with DCM and filtered through silica gel. The volatiles were removed under vacuum, and flash chromatography (gradient 0-30% dichloromethane in hexanes) was used to purify the product. The curde product obtained from chromatography was further purified by trituration with methanol. Yield: 0.100 g, 39%.

In a 20-mL glass tube equipped with a screw cap, was placed p-CP—Br/Trz (0.104 g), TTC-Cz (0.062 g), NaO$^t$Bu (0.025 g), Pd$_2$(dba)$_3$ (0.037 g) and tBuXPhos (0.051 g). The tube was evacuated/refilled with argon three times and then added 1,4-dioxane (1.0 mL) under argon. The mixture was stirred at 110° C. for 1 d. For work-up, the mixture was diluted with DCM and filtered through silica gel. The volatiles were removed under vacuum, and flash chromatography (gradient 0-30% dichloromethane in hexanes) was used to purify the product. The curde product obtained from chromatography was further purified by trituration with methanol. Yield: 0.065 g, 42%.

Scheme 20. Synthesis of p-CP-(N-TTC-Cz)/Trz

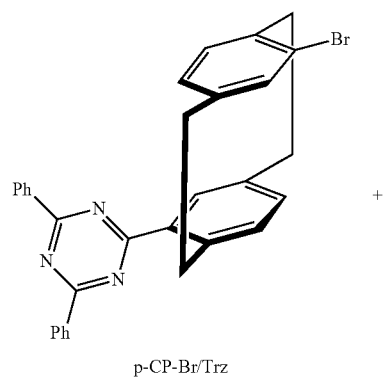

p-CP-Br/Trz

+

Scheme 21. Synthesis of p-CP-(N-Poz)/Trz

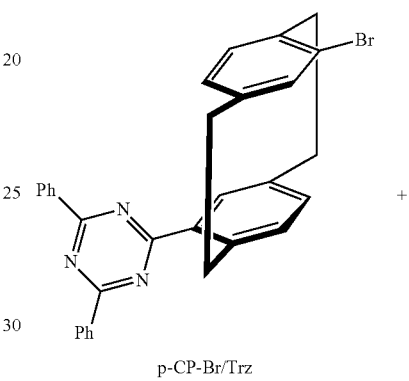

p-CP-Br/Trz

+

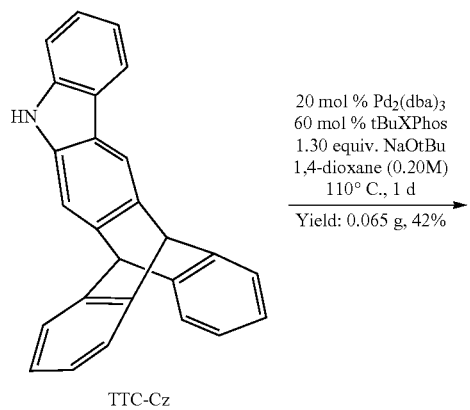

TTC-Cz 20 mol % Pd$_2$(dba)$_3$
60 mol % tBuXPhos
1.30 equiv. NaOtBu
1,4-dioxane (0.20M)
110° C., 1 d
Yield: 0.065 g, 42%

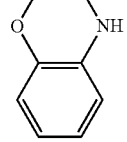

20 mol % Pd$_2$(dba)$_3$
60 mol % XPhos
1.50 equiv. NaOtBu
1,4-dioxane (0.20M)
110° C., 1 d
Yield: 0.028 g, 50%

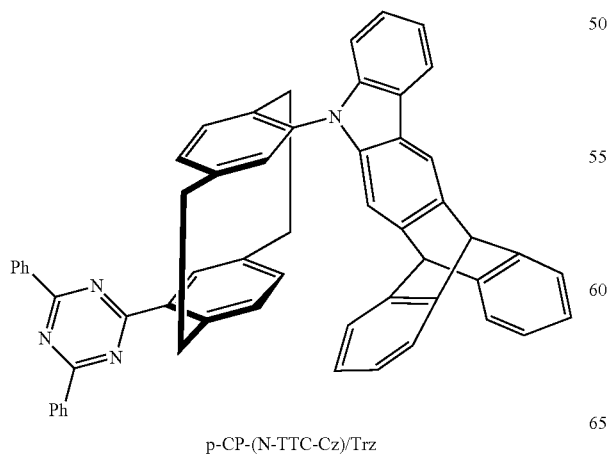

p-CP-(N-TTC-Cz)/Trz

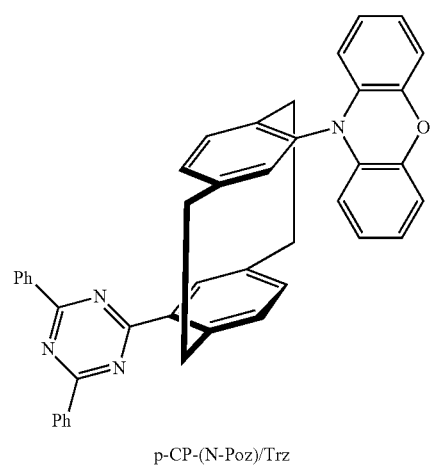

p-CP-(N-Poz)/Trz

In a 20-mL glass tube equipped with a screw cap, was placed p-CP—Br/Trz (0.052 g), phenoxazine (0.017 g), NaO$^t$Bu (0.014 g), Pd$_2$(dba)$_3$ (0.018 g) and XPhos (0.029 g). The tube was evacuated/refilled with argon three times and then added 1,4-dioxane (0.5 mL) under argon. The mixture was stirred at 110° C. for 1 d. For work-up, the mixture was diluted with DCM and filtered through silica gel. The volatiles were removed under vacuum, and flash chromatography (gradient 0-30% dichloromethane in hexanes) was used to purify the product. Yield: 0.028 g, 50%.

In a 20-mL glass tube equipped with a screw cap, was placed p-CP—Br/Trz (0.052 g), phenoxazine (0.017 g), NaO$^t$Bu (0.014 g), Pd$_2$(dba)$_3$ (0.028 g) and XPhos (0.043 g). The tube was evacuated/refilled with argon three times and then added 1,4-dioxane (0.5 mL) under argon. The mixture was stirred at 110° C. for 1 d. For work-up, the mixture was diluted with DCM and filtered through silica gel. The volatiles were removed under vacuum, and flash chromatography (gradient 0-30% dichloromethane in hexanes) was used to purify the product. Yield: 0.010 g, 19%.

Scheme 22. Synthesis of p-CP-(N-Ard)/Trz

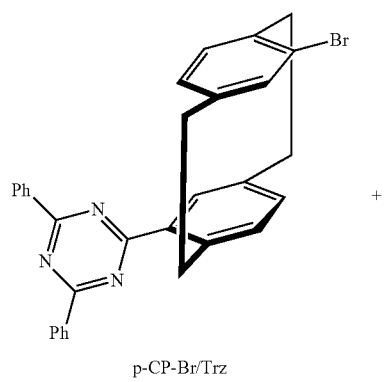

p-CP-Br/Trz

Scheme 23. Synthesis of o-CP-NPh$_2$/Trz

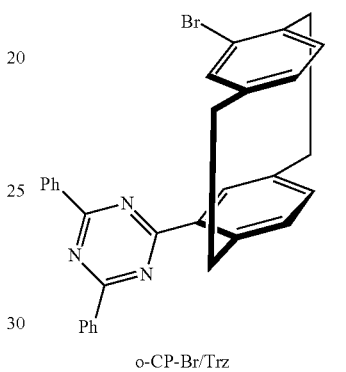

o-CP-Br/Trz

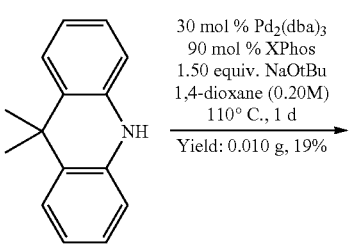

30 mol % Pd$_2$(dba)$_3$
90 mol % XPhos
1.50 equiv. NaOtBu
1,4-dioxane (0.20M)
110° C., 1 d
Yield: 0.010 g, 19%

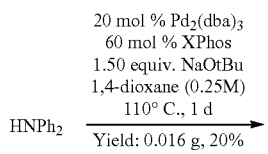

HNPh$_2$ 20 mol % Pd$_2$(dba)$_3$
60 mol % XPhos
1.50 equiv. NaOtBu
1,4-dioxane (0.25M)
110° C., 1 d
Yield: 0.016 g, 20%

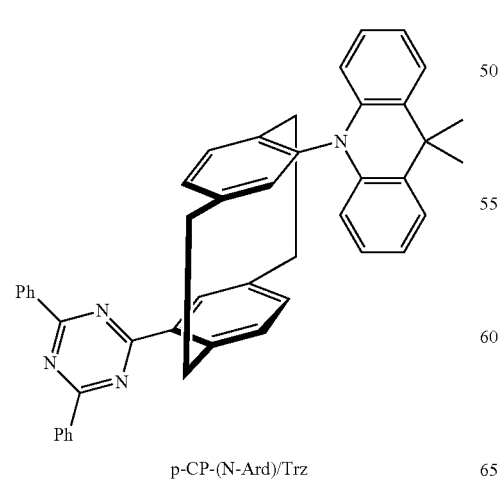

p-CP-(N-Ard)/Trz

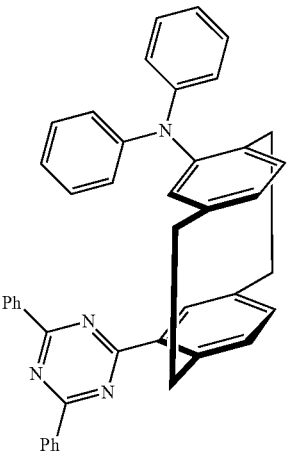

o-CP-NPh$_2$/Trz

In a 20-mL glass tube equipped with a screw cap, was placed o-CP—Br/Trz (0.052 g), diphenylamine (0.019 g), NaO$^t$Bu (0.014 g), Pd$_2$(dba)$_3$ (0.028 g) and XPhos (0.043 g). The tube was evacuated/refilled with argon three times and then added 1,4-dioxane (0.5 mL) under argon. The mixture was stirred at 110° C. for 1 d. For work-up, the mixture was diluted with DCM and filtered through silica gel. The volatiles were removed under vacuum, and flash chromatography (gradient 0-20% dichloromethane in hexanes) was used to purify the product. Yield: 0.016 g, 20%.

Example 3—Compounds where Donor/Acceptor Interact Via Spatial Proximity

Table 6 depicts compounds that involve a donor (top ring)-acceptor (heteroaromatic group) interaction through spatial proximity.

TABLE 6

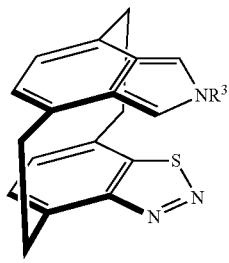

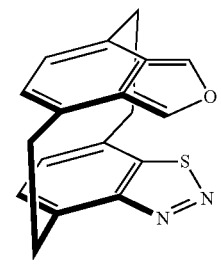

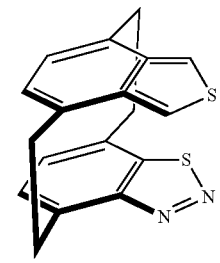

TABLE 6-continued

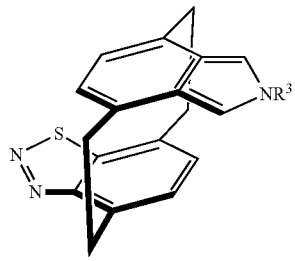

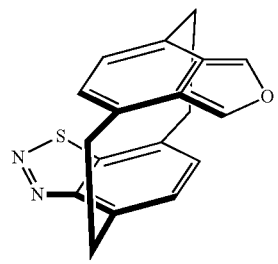

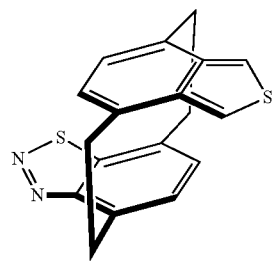

Example 4—Polymeric Materials for Single Color Light OLED Applications

[2.2]paracylophane is a dimer of p-xylylene which can polymerize to form parylene, a trade name for variety poly(p-xylylene) polymers. The process is "green" polymer chemistry because, under pyrolysis conditions (usually heat and vacuum), [2.2]paracyclophane yields 100% monomer, i.e., p-xylylene, with no by-products.

By anaology, we anticipate that [2.2]paracyclophane derived N-arylated carbazoles will undergo similar process (Gorham Process) and yield poly(carbazole) polymers, thereby forming homogeneous polymeric carbazole-based OLED materials, as depicted in Scheme 15. See Gorham, W. F. (1966), A New, General Synthetic Method for the Preparation of Linear Poly-p-xylylenes. *J. Polym. Sci. A*-1 *Polym. Chem.*, 4: 3027-3039.

Scheme 24

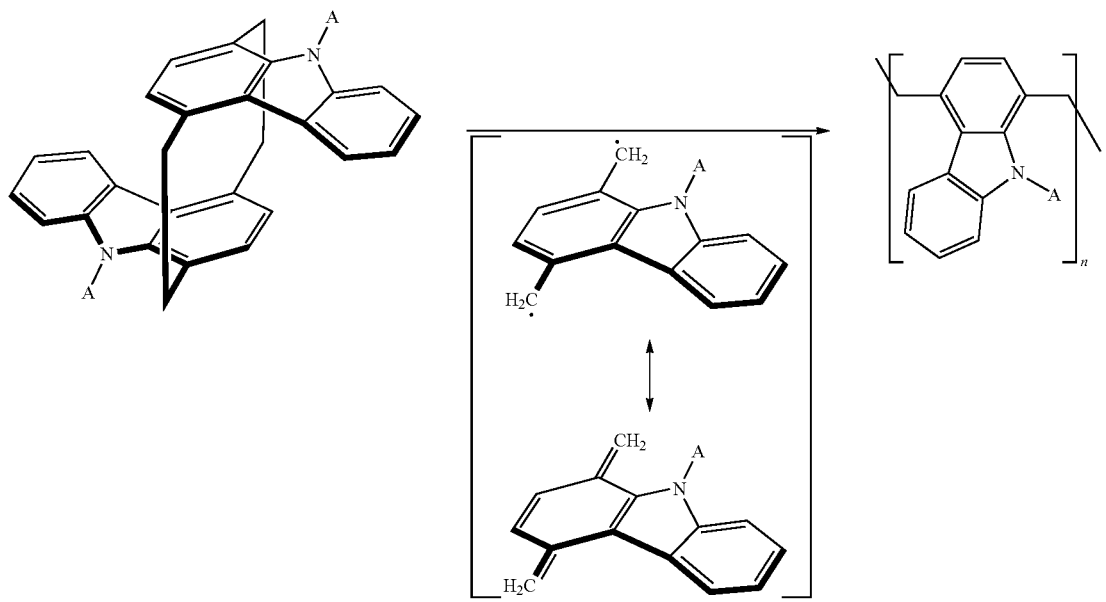

Example 5—Polymeric Materials for White Light OLED Applications

[2.2]paracylophane is a dimer of p-xylylene which can polymerize to form parylene, a trade name for variety poly(p-xylylene) polymers. The process is "green" polymer chemistry because, under pyrolysis conditions (usually heat and vacuum), [2.2]paracyclophane yields 100% monomer, i.e., p-xylylene, with no by-products.

By anaology, we anticipate that asymmetrically-substituted [2.2]paracyclophane derived N-arylated carbazoles will undergo similar process (Gorham Process) and yield poly(carbazole) polymers, thereby forming heterogeneous polymeric carbazole-based OLED materials, as depicted in Scheme 16. See Gorham, W. F. (1966), A New, General Synthetic Method for the Preparation of Linear Poly-p-xylylenes. *J. Polym. Sci. A-1 Polym. Chem.*, 4: 3027-3039. In the resulting polymer, the different repeat units may be randomly distributed or in a certain order. By tuning identity of $R_x$ and $R_y$, and relative concentrations of starting materials, the resulting polymers may be white light emitters.

Scheme 25

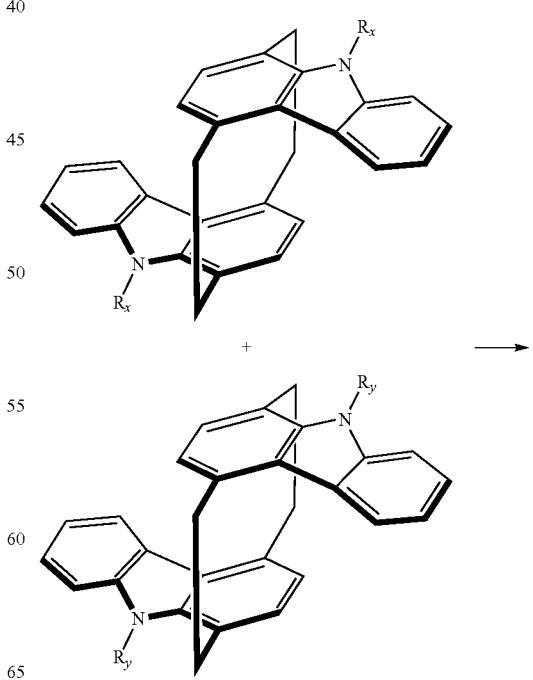

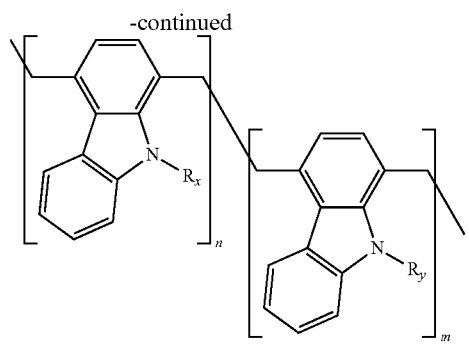

Example 6—Prophetic Syntheses of Compounds where Donor/Acceptor Interact Via Spatial Proximity Scheme 26. Synthesis of p-CP-NPh₂/Pmd

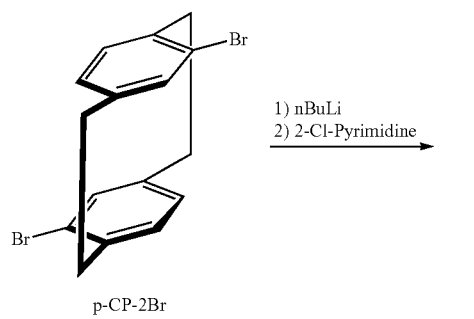

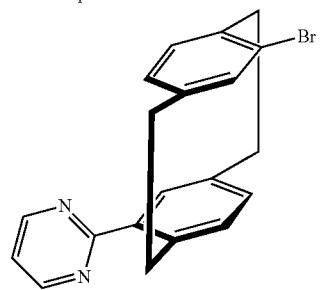

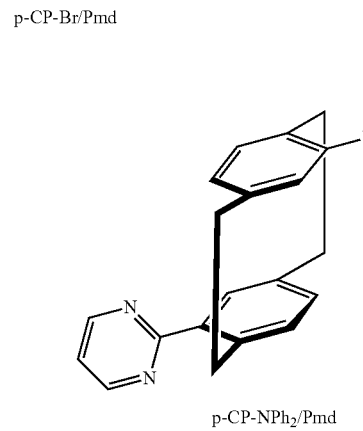

p-CP-2Br to p-CP—Br/Pmd: In a 500-mL round-bottom flask, is added p-CP-2Br (1.2 equiv.) and 250 mL of anhydrous THF. The solution is placed in dry ice/acetone bath for 15 min before dropwisely adding nBuLi (2.5 M in n-hexane, 1.3 equiv.) to result in a yellow slurry. The reaction mixture is allowed to stir at −78° C. for 0.5 h. Then THF solution (30 mL) of 2-chloropyrimidine (1.0 equiv.) is slowly transferred into the yellow slurry over a period of 5 min. After addition, the mixture is allowed to warm up to room temperature and stirred for 12 h. For work-up, the reaction mixture is quenched by saturated NH₄Cl solution and organic layer is washed by NH₄Cl solution twice followed by saturated NaCl twice and dried over MgSO₄. After removing volatiles, the crude product is purified by flash chromatography (gradient 0-20% DCM in hexanes).

p-CP—Br/Pmd to p-CP—NPh₂/Pmd: In a 20 mL reaction tube equipped with Teflon cap, are added p-CP—Br/Pmd (1.0 equiv.), NaO$^t$Bu (1.3 equiv.), diphenylamine (0.85 equiv.), Pd₂(dba)₃ (20 mol % [Pd]), and XPhos (30 mol %). The flask is evacuated/refilled with argon three times and then 1,4-dioxane (0.2 M for p-CP—Br/Pmd) is transferred under argon. The mixture is stirred at 110° C. for 1 d. For work-up, the mixture is diluted with ethyl acetate and then filtered through silica gel. After removing the volatiles of the filtrate, flash chromatography (gradient 0-30% dichloromethane in hexanes) is used to purify the product.

Scheme 27. Synthesis of p-CP-NPh₂/Ipn

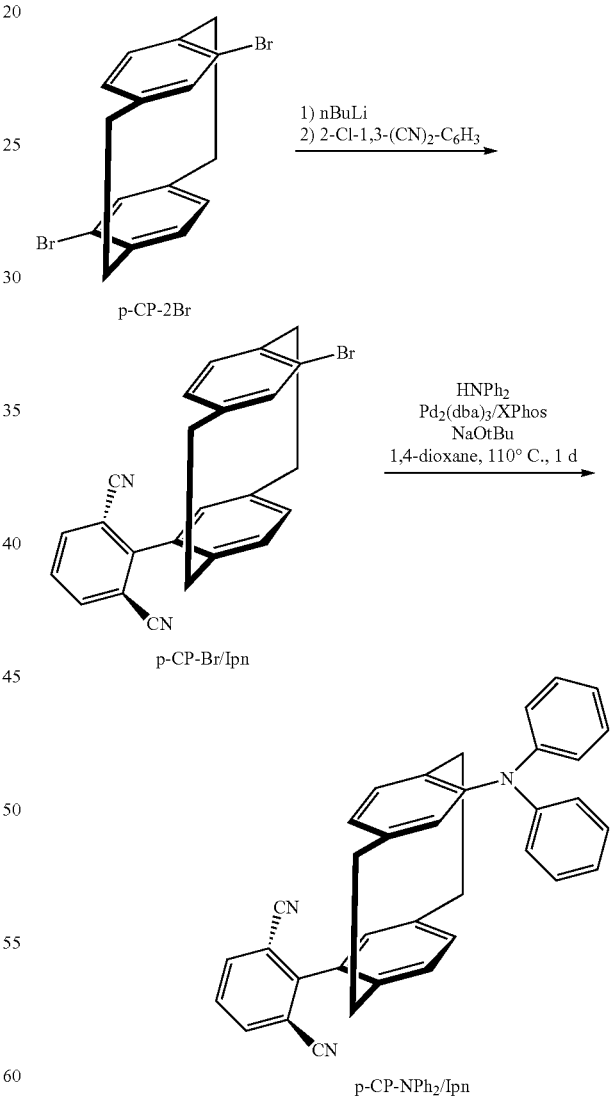

p-CP-2Br to p-CP—Br/Ipn: In a 500-mL round-bottom flask, is added p-CP-2Br (1.2 equiv.) and 250 mL of anhydrous THF. The solution is placed in dry ice/acetone bath for 15 min before dropwisely adding nBuLi (2.5 M in n-hexane, 1.3 equiv.) to result in a yellow slurry. The reaction mixture is allowed to stir at −78° C. for 0.5 h. Then THF solution (30 mL) of 2-chloroisophthalonitrile (1.0 equiv.) is slowly transferred into the yellow slurry over a period of 5 min. After addition, the mixture is allowed to warm up to room temperature and stirred for 12 h. For work-up, the reaction mixture is quenched by saturated NH$_4$Cl solution and organic layer is washed by NH$_4$Cl solution twice followed by saturated NaCl twice and dried over MgSO$_4$. After removing volatiles, the crude product is purified by flash chromatography (gradient 0-20% DCM in hexanes).

p-CP—Br/Ipn to p-CP—NPh$_2$/Ipn: In a 20 mL reaction tube equipped with Teflon cap, are added p-CP—Br/Ipn (1.0 equiv.), NaO$^t$Bu (1.3 equiv.), diphenylamine (0.85 equiv.), Pd$_2$(dba)$_3$ (20 mol % [Pd]), and XPhos (30 mol %). The flask is evacuated/refilled with argon three times and then 1,4-dioxane (0.2 M for p-CP—Br/Ipn) is transferred under argon. The mixture is stirred at 110° C. for 1 d. For work-up, the mixture is diluted with ethyl acetate and then filtered through silica gel. After removing the volatiles of the filtrate, flash chromatography (gradient 0-30% dichloromethane in hexanes) is used to purify the product.

stirred at 100° C. for 1 d. For work-up, the mixture is diluted with ethyl acetate and then filtered through silica gel. After removing the volatiles of the filtrate, flash chromatography (gradient 0-20% dichloromethane in hexanes) is used to purify the product.

p-CP—Br/(p-Py) to p-CP—(N-Cz)/(p-Py): In a 20 mL reaction tube equipped with Teflon cap, are added p-CP—Br/(p-Py) (1.0 equiv.), NaO$^t$Bu (1.3 equiv.), carbazole (0.85 equiv.), Pd$_2$(dba)$_3$ (20 mol % [Pd]), and XPhos (30 mol %). The flask is evacuated/refilled with argon three times and then 1,4-dioxane (0.2 M for p-CP—Br/(p-Py)) is transferred under argon. The mixture is stirred at 110° C. for 1 d. For work-up, the mixture is diluted with ethyl acetate and then filtered through silica gel. After removing the volatiles of the filtrate, flash chromatography (gradient 0-30% dichloromethane in hexanes) is used to purify the product.

Scheme 28. Synthesis of p-CP-(N-Cz)/(p-Py)

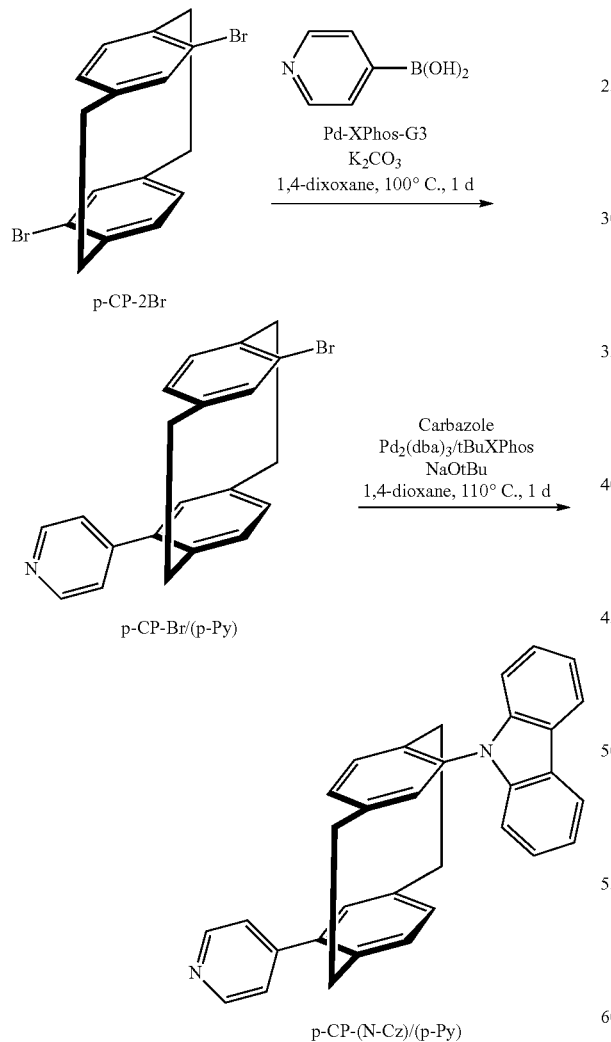

Scheme 29. Synthesis of p-CP-(N-Cz)/(3,5-C$_6$H$_3$(CF$_3$)$_2$)

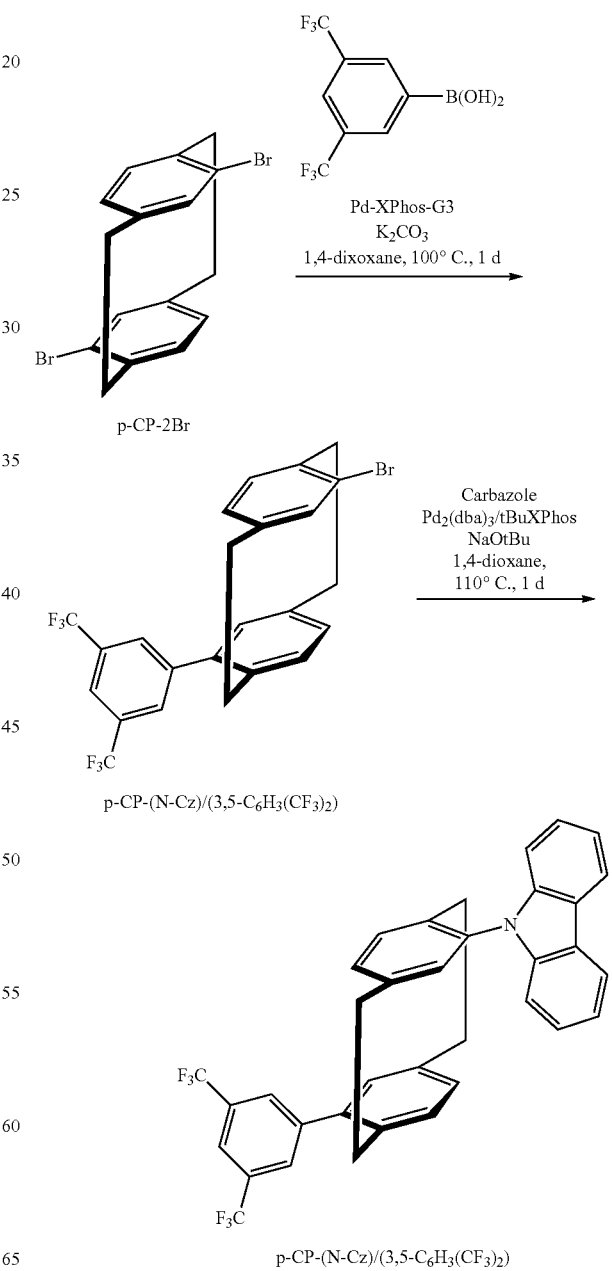

p-CP-2Br to p-CP—Br/(p-Py): In a 20 mL reaction tube equipped with Teflon cap, are added p-CP-2Br (1.0 equiv.), K$_2$CO$_3$ (3.0 equiv.), 4-pyridineboronic acid (1.2 equiv.), and Pd-XPhos-G3 precatalyst (5 mol %). The flask is evacuated/refilled with argon three times and then 1,4-dioxane (0.2 M for p-CP-2Br) is transferred under argon. The mixture is p-CP-2Br to p-CP—Br/(3,5-C$_6$H$_3$(CF$_3$)$_2$): In a 20 mL reaction tube equipped with Teflon cap, are added p-CP-2Br (1.0 equiv.), K$_2$CO$_3$ (3.0 equiv.), 3,5-bis(trifluoromethyl)benzeneboronic acid (1.2 equiv.), Pd-XPhos-G3 precatalyst (5 mol %). The flask is evacuated/refilled with argon three times and then 1,4-dioxane (0.2 M for p-CP-2Br) is transferred under argon. The mixture is stirred at 100° C. for 1 d. For work-up, the mixture is diluted with ethyl acetate and then filtered through silica gel. After removing the volatiles of the filtrate, flash chromatography (gradient 0-20% dichloromethane in hexanes) is used to purify the product.

p-CP—Br/(3,5-C$_6$H$_3$(CF$_3$)$_2$) to p-CP—(N-Cz)/(3,5-C$_6$H$_3$(CF$_3$)$_2$): In a 20 mL reaction tube equipped with Teflon cap, are added p-CP—Br/(3,5-C$_6$H$_3$(CF$_3$)$_2$) (1.0 equiv.), NaO$^t$Bu (1.3 equiv.), carbazole (0.85 equiv.), Pd$_2$(dba)$_3$ (20 mol % [Pd]), and XPhos (30 mol %). The flask is evacuated/refilled with argon three times and then 1,4-dioxane (0.2 M for p-CP—Br/(3,5-C$_6$H$_3$(CF$_3$)$_2$)) is transferred under argon. The mixture is stirred at 110° C. for 1 d. For work-up, the mixture is diluted with ethyl acetate and then filtered through silica gel. After removing the volatiles of the filtrate, flash chromatography (gradient 0-30% dichloromethane in hexanes) is used to purify the product.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound
(a) of formula Ia or formula Ib:

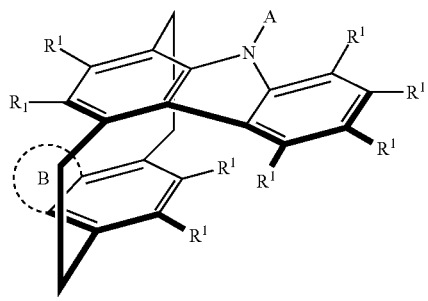

Formula Ia

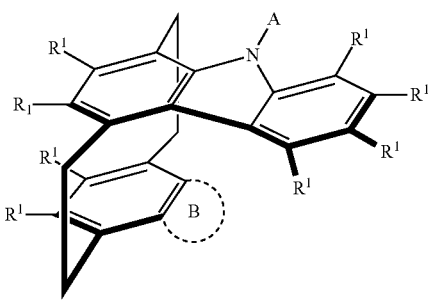

Formula Ib wherein
A is an aromatic moiety substituted with at least one electron-withdrawing substituent or a heteroaromatic moiety substituted with at least one electron-withdrawing substituent;

R$^1$ is, independently for each occurrence, hydrogen or alkyl; and
B is absent or an optionally substituted heteroaromatic moiety;

(b) of formula IIa', formula IIb', or formula IIc':

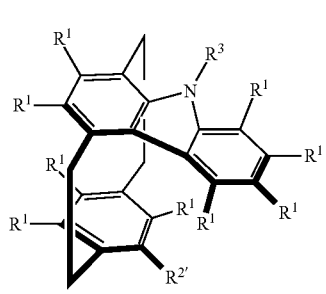

Formula IIa'

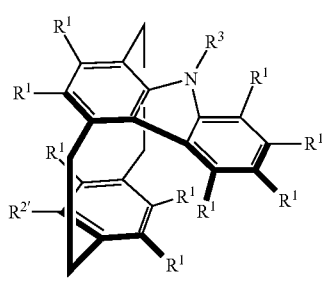

Formula IIb'

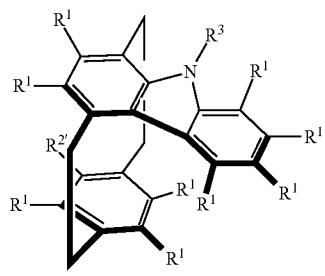

Formula IIc' wherein
R$^1$ is, independently for each occurrence, hydrogen or alkyl;
R$^{2'}$ is substituted or unsubstituted triazinyl, substituted or unsubstituted phenyl, substituted or unsubstituted pyridyl, substituted or unsubstituted pyrimidyl, or an electron-withdrawing group; and
R$^3$ is hydrogen, alkyl, an optionally substituted aromatic moiety, or an optionally substituted heteroaromatic moiety;

(c) of formula IIIa', formula IIIb', or formula IIIc':

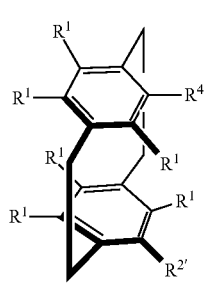

Formula IIIa'

-continued

Formula IIIb'

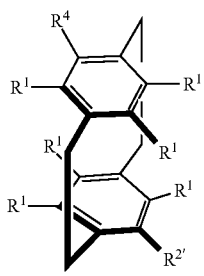

Formula IIIc'

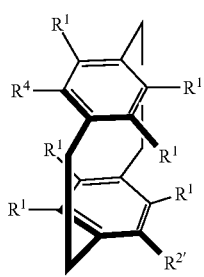

wherein
R¹ is, independently for each occurrence, hydrogen or alkyl;
R²' is substituted or unsubstituted triazinyl, substituted or unsubstituted phenyl, substituted or unsubstituted pyridyl, substituted or unsubstituted pyrimidyl, or an electron-withdrawing group; and
R⁴ is hydrogen or an electron-donating group;

(d) of formula IVa or formula IVb:

Formula IVa

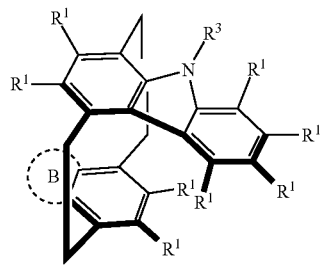

Formula IVb

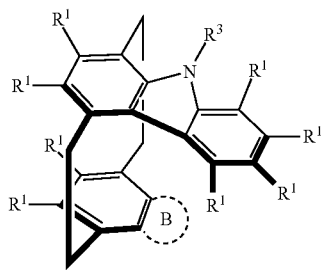

wherein
R¹ is, independently for each occurrence, hydrogen or alkyl;
B is absent or an optionally substituted heteroaromatic moiety; and
R³ is hydrogen, alkyl, an optionally substituted aromatic moiety, or an optionally substituted heteroaromatic moiety; or (e) of formula Va or formula Vb:

Formula Va

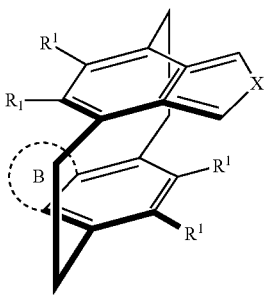

Formula Vb

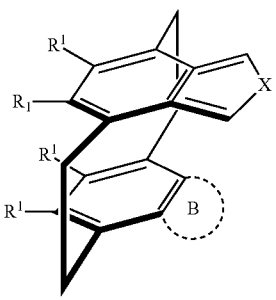

wherein
R¹ is, independently for each occurrence, hydrogen or alkyl;
B is absent or an optionally substituted heteroaromatic moiety;
X is O, S, or NR³; and
R³ is hydrogen, alkyl, an optionally substituted aromatic moiety, or an optionally substituted heteroaromatic moiety.

2. The compound of claim 1, wherein the compound is a compound of formula Ia or formula Ib; and A is an aromatic moiety substituted with at least one electron-withdrawing substituent.

3. The compound of claim 1, wherein the compound is a compound of formula Ia or formula Ib; and A is a heteroaromatic moiety substituted with at least one electron-withdrawing substituent.

4. The compound of claim 1, wherein the compound is a compound of formula Ia or formula Ib; and A is phenyl substituted with at least one electron-withdrawing substituent.

5. The compound of claim 1, wherein the compound is a compound of formula Ia or formula Ib, a compound of formula IVa or formula IVb, or a compound of formula Va or formula Vb; and B is absent.

6. The compound of claim 1, wherein the compound is a compound of formula Ia or formula Ib, a compound of formula IVa or formula IVb, or a compound of formula Va or formula Vb; and the B-ring is derived from an acridine, carbazole, carboline, cinnoline, furan, furazan, imidazole, indazole, indole, indolizine, isobenzofuran, isoindole, isoquinoline, isothiazole, isoxazole, naphthyridine, oxazole, phenanthridine, phenanthroline, phenazine, phthalazine, pteridine, purine, pyrazine, pyrazole, pyridazine, pyridine, pyrimidine, pyrrole, quinazoline, quinoline, quinoxaline, thiadiazole, thianthrene, thiophene, triazole, or trithiole.

7. The compound of claim 1, wherein the compound is a compound of formula Ia or formula Ib, a compound of formula IVa or formula IVb, or a compound of formula Va or formula Vb; and the B-ring is

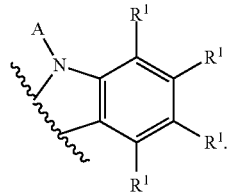

8. The compound of claim 1, wherein R¹ is hydrogen.

9. The compound of claim 1, wherein R¹ is methyl, ethyl, propyl, or butyl.

10. The compound of claim 1, wherein the compound is a compound of formula IIa', formula IIb', or formula IIc', or a compound of formula IIIa', formula IIIb', or formula IIIc'; and $R^{2'}$ is substituted or unsubstituted triazinyl.

11. The compound of claim 1, wherein the compound is a compound of formula IIa', formula IIb', or formula IIc', or a compound of formula IVa or formula IVb, or a compound of formula Va or formula Vb; and $R^3$ is hydrogen.

12. The compound of claim 1, wherein the compound is a compound of formula IIa', formula IIb', or formula IIc', or a compound of formula IVa or formula IVb, or a compound of formula Va or formula Vb; and $R^3$ is methyl, ethyl, propyl, or butyl.

13. The compound of claim 1, wherein the compound is a compound of formula IIa', formula IIb', or formula IIc', or a compound of formula IVa or formula IVb, or a compound of formula Va or formula Vb; and $R^3$ is an unsubstituted aromatic moiety or an unsubstituted heteroaromatic moiety.

14. The compound of claim 1, wherein the compound is a compound of formula IIa', formula IIb', or formula IIc', or a compound of formula IVa or formula IVb, or a compound of formula Va or formula Vb; and $R^3$ is phenyl.

15. The compound of claim 1, wherein the compound is a compound of formula IIa', formula IIb', or formula IIc', or a compound of formula IVa or formula IVb, or a compound of formula Va or formula Vb; and $R^3$ is a substituted heteroaromatic moiety.

16. The compound of claim 1, wherein the compound is a compound of formula IIa', formula IIb', or formula IIc', or a compound of formula IVa or formula IVb, or a compound of formula Va or formula Vb; and $R^3$ is an aromatic moiety substituted with at least one electron-withdrawing substituent.

17. The compound of claim 1, wherein the compound is a compound of formula IIa', formula IIb', or formula IIc', or a compound of formula IVa or formula IVb, or a compound of formula Va or formula Vb; and $R^3$ is phenyl substituted with at least one electron-withdrawing substituent.

18. The compound of claim 1, wherein the compound is a compound of formula IIa', formula IIb', or formula IIc', or a compound of formula IVa or formula IVb, or a compound of formula Va or formula Vb; and $R^3$ is an aromatic moiety substituted with at least one alkyl, aryl, or aralkyl substituent.

19. The compound of claim 1, wherein the compound is a compound of formula IIa', formula IIb', or formula IIc', or a compound of formula IVa or formula IVb, or a compound of formula Va or formula Vb; and $R^3$ is phenyl substituted with at least one alkyl, aryl, or aralkyl substituent.

20. The compound of claim 1, wherein the compound is a compound of formula IIIa', formula IIIb', or formula IIIc'; and $R^4$ is hydrogen.

21. The compound of claim 1, wherein the compound is a compound of formula IIIa', formula IIIb', or formula IIIc'; and $R^4$ is —NH₂, —NHR″, —N(R″)₂, —OH, —OR″, —NR″C(O)R″, —NHC(O)R″, or —OC(O)R″, wherein R″ is alkyl, aryl, or aralkyl.

22. The compound of claim 1, wherein the compound is a compound of a compound of formula Va or formula Vb; and X is O.

23. The compound of claim 1, wherein the compound is a compound of a compound of formula Va or formula Vb; and X is S.

24. The compound of claim 1, wherein the compound is a compound of a compound of formula Va or formula Vb; and X is $NR^3$.

25. An electronic device, such as an OLED, comprising an anode, a cathode, and an emissive layer, wherein the emissive layer is disposed between the anode and the cathode; and the emissive layer comprises a compound of claim 1.

26. A method of producing visible light, comprising applying a charge to an electronic device of claim 25.

* * * * *